(12) United States Patent
Kwon et al.

(10) Patent No.: US 11,357,104 B2
(45) Date of Patent: Jun. 7, 2022

(54) GARMENT-TYPE ELECTRONIC DEVICE AND METHOD FOR PRODUCING SAME

(71) Applicant: TOYOBO CO., LTD., Osaka (JP)

(72) Inventors: Euichul Kwon, Shiga (JP); Sonoko Ishimaru, Shiga (JP); Michihiko Irie, Shiga (JP); Maki Kinami, Shiga (JP)

(73) Assignee: TOYOBO CO., LTD., Osaka (JP)

( * ) Notice: Subject to any disclaimer, the term of this patent is extended or adjusted under 35 U.S.C. 154(b) by 58 days.

(21) Appl. No.: 17/021,431

(22) Filed: Sep. 15, 2020

(65) Prior Publication Data

US 2021/0007223 A1 Jan. 7, 2021

Related U.S. Application Data

(62) Division of application No. 16/076,766, filed as application No. PCT/JP2017/003201 on Jan. 30, 2017, now Pat. No. 10,869,391.

(30) Foreign Application Priority Data

Feb. 12, 2016 (JP) .................................. 2016-024716
Feb. 12, 2016 (JP) .................................. 2016-024717
(Continued)

(51) Int. Cl.
*H05K 1/02* (2006.01)
*H05K 1/03* (2006.01)
(Continued)

(52) U.S. Cl.
CPC .............. *H05K 1/092* (2013.01); *A41D 1/00* (2013.01); *A41D 1/005* (2013.01); *A41D 13/00* (2013.01);
(Continued)

(58) Field of Classification Search
CPC .......... A41D 1/00; A41D 1/002; A41D 1/005; A41D 13/00; A61B 5/25; A61B 5/291;
(Continued)

(56) References Cited

U.S. PATENT DOCUMENTS

| 8,386,009 B2 | 2/2013 | Lindberg |
| 9,808,196 B2 | 11/2017 | Macia Barber et al. |

(Continued)

FOREIGN PATENT DOCUMENTS

| JP | 2-234901 | 9/1990 |
| JP | 03-207341 | 9/1991 |

(Continued)

OTHER PUBLICATIONS

Notice of Reasons for Refusal dated Jan. 5, 2021 in corresponding Japanese Patent Application No. 2017-566585, with Machine Translation.

(Continued)

*Primary Examiner* — Nathan Milakovich
(74) *Attorney, Agent, or Firm* — Wenderoth, Lind & Ponack, L.L.P.

(57) ABSTRACT

The purpose of the present invention is to provide a garment-type electronic device capable of reducing discomfort during the wearing in the garment-type electronic device comprising an electrical wiring using stretchable conductor composition. In a part in contact with a body surface of a garment-type electronic device, a level difference at the boundary between the electrode portion where the conductor is exposed and the wiring portion covered with the insulating cover layer is substantially eliminated, whereby a garment type electronic device with a natural wearing feeling in which discomfort during wearing has been reduced is obtained. Furthermore, by providing the projections and the depressions in the fabric texture on its surface, a more
(Continued)

natural wearing feeling is obtained. Such a garment-type electronic device can be produced by a printing transfer method.

8 Claims, 5 Drawing Sheets

(30) Foreign Application Priority Data

Feb. 12, 2016 (JP) .................................. 2016-024718
Nov. 18, 2016 (JP) .................................. 2016-225145
Nov. 18, 2016 (JP) .................................. 2016-225146
Nov. 18, 2016 (JP) .................................. 2016-225147

(51) Int. Cl.
| | | |
|---|---|---|
| *H05K 1/09* | (2006.01) | |
| *H05K 1/11* | (2006.01) | |
| *H05K 1/18* | (2006.01) | |
| *A41D 1/00* | (2018.01) | |
| *A41D 13/00* | (2006.01) | |
| *H05K 3/20* | (2006.01) | |
| *A61B 5/25* | (2021.01) | |
| *A61B 5/291* | (2021.01) | |

(52) U.S. Cl.
CPC ................ *A61B 5/25* (2021.01); *A61B 5/291* (2021.01); *H05K 1/0298* (2013.01); *H05K 1/038* (2013.01); *H05K 1/185* (2013.01); *H05K 3/207* (2013.01); *H05K 1/118* (2013.01); *H05K 1/189* (2013.01); *H05K 2201/0323* (2013.01); *H05K 2203/0191* (2013.01)

(58) Field of Classification Search
CPC .... A61B 5/6804; H05K 1/0298; H05K 1/038; H05K 1/092; H05K 1/118; H05K 1/185; H05K 1/189; H05K 2201/0323; H05K 2203/0191; H05K 3/207; H05K 3/28
See application file for complete search history.

(56) References Cited

U.S. PATENT DOCUMENTS

| | | |
|---|---|---|
| 10,034,382 B2 | 7/2018 | Yan |
| 11,130,888 B2* | 9/2021 | Kwon .................... C09J 201/00 |
| 2007/0254456 A1 | 11/2007 | Maruyama et al. |
| 2010/0234715 A1 | 9/2010 | Shin |
| 2013/0123601 A1 | 5/2013 | Lindberg et al. |
| 2013/0338472 A1 | 12/2013 | Maciá Barber et al. |
| 2017/0213648 A1* | 7/2017 | Joyce .................. H01F 27/2804 |

FOREIGN PATENT DOCUMENTS

| | | |
|---|---|---|
| JP | 3723565 | 12/2005 |
| JP | 2007-173226 | 7/2007 |
| JP | 2012-54192 | 3/2012 |
| JP | 2013-258419 | 12/2013 |

OTHER PUBLICATIONS

International Search Report dated Apr. 18, 2017 in International (PCT) Application No. PCT/JP2017/003201.
Ahn et al., "Stretchable electronics: materials, architectures and integrations", Journal of Physics D: Applied Physics, vol. 45, 2012, 14 pages.
Office Action dated Jul. 26, 2019 in corresponding Chinese Patent Application No. 201780010946.8, with English translation.
Extended European Search Report dated Sep. 11, 2019 in corresponding European Patent Application No. 17750113.7.
Office Action dated Mar. 11, 2020 in corresponding Chinese Patent Application No. 201780010946.8 with English-language translation.
MatWeb, Fluorosilicone Rubber (FMQ, FVMQ, FSi), retrieved from http://www.matweb.com/search/DataSheet.aspx?MatGUID=5a39836207ff4b72acc19d1ab8099830, 2019.
MatWeb, Overview of materials for Silicone Rubber, retrieved from http://www.matweb.com/search/DataSheet.aspx?MatGUID=cbe7a469897a47eda563816c86a73520, 2019.
Chinese Decision of Rejection dated Jul. 31, 2020 in corresponding Chinese Patent Application No. 201780010946.8, with English Translation.
Office Action dated Oct. 29, 2021 in corresponding European Patent Application No. 17750113.7.
Notification of Reexamination dated Jan. 14, 2022 in corresponding Chinese Patent Application No. 201780010946.8, with English Translation.
Examination Decision of the Patent Reexamination Board dated Mar. 30, 2022 in Chinese Application No. 20170010946.8, with English translation.

* cited by examiner

PRIOR ART
[Fig. 1]
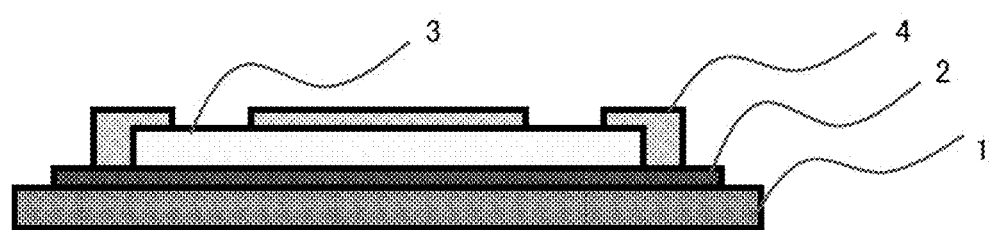
PRIOR ART
[Fig. 2]
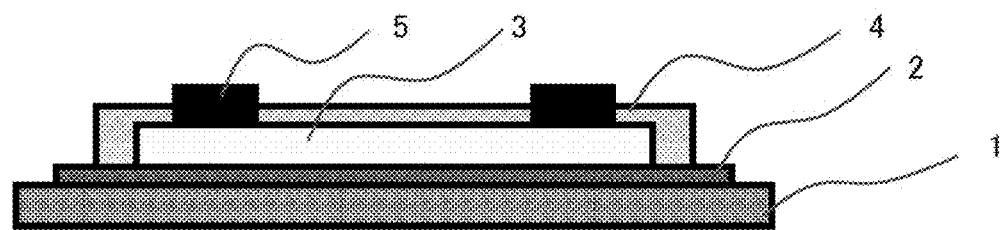

[Fig. 3]
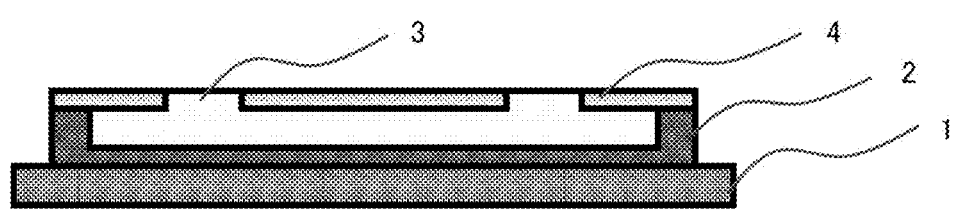
[Fig. 4]
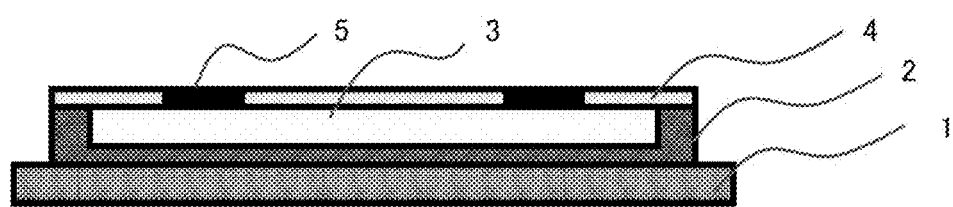

[Fig. 5]
Temporary support body (releasing support body) — 10
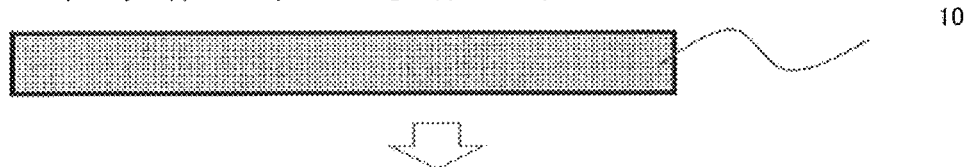
Temporarily fixing fabric (substrate) — 1
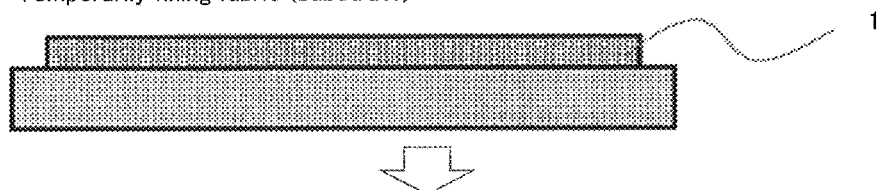
Printing stretchable conductor layer — 3
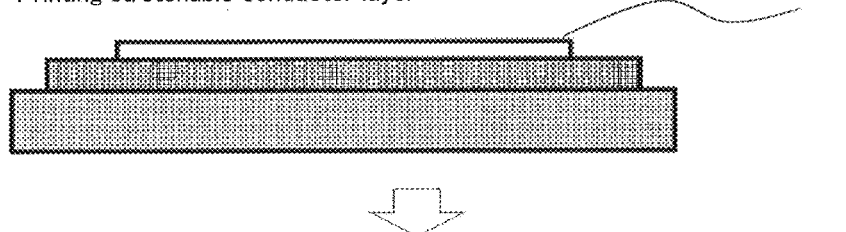
Printing stretchable cover layer (insulating cover layer) — 4
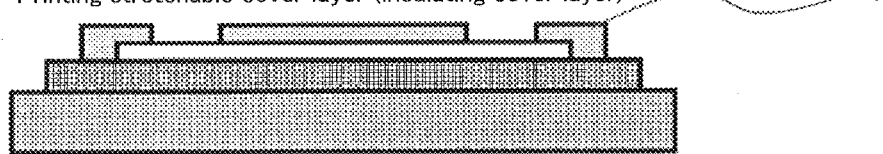
Printing stretchable carbon layer (electrode surface layer) — 5
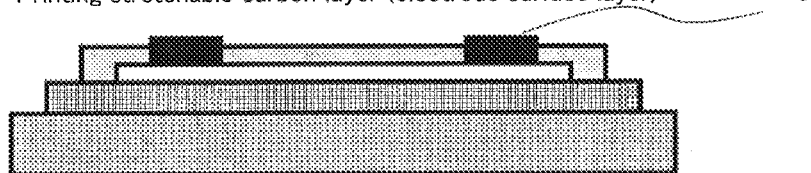
peeling off temporary support body
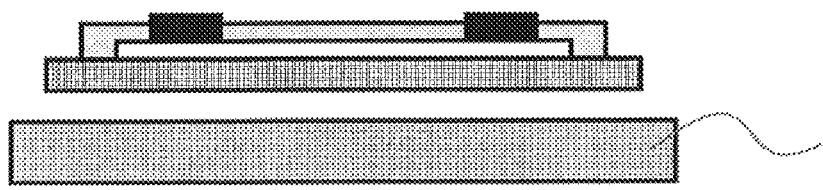
10

[Fig. 6]
releasing support body
 10
Printing stretchable carbon layer (electrode surface layer)
 5
Printing stretchable cover layer (insulating cover layer)
 4
Printing stretchable conductor layer
 3
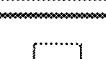
Printing adhesive layer
 7
Bonding fabric (substrate)
 1
Peeling off releasing support body
 10

[Fig. 7]
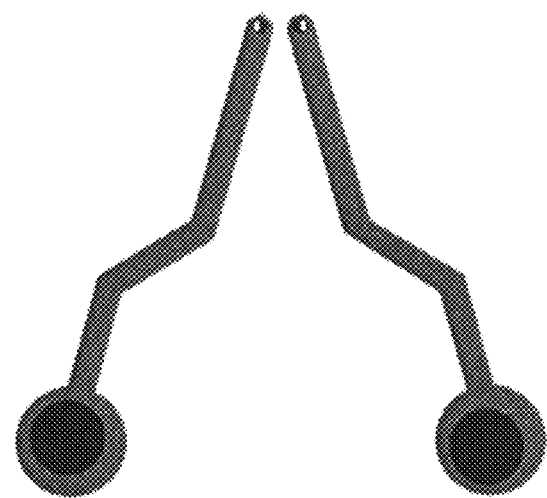
[Fig. 8]
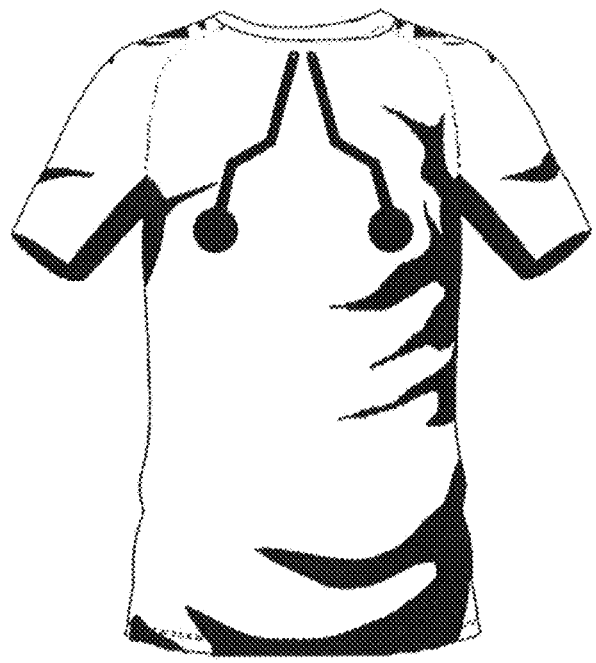

GARMENT-TYPE ELECTRONIC DEVICE AND METHOD FOR PRODUCING SAME

TECHNICAL FIELD

The present invention relates to a garment-type wearable electronic device that is used with an electronic function or an electric function being incorporated into a garment. In particular, the present invention relates to a garment-type electronic device including a stretchable electrical wiring and having a natural wearing feeling, and a method for producing the same.

BACKGROUND ART

Recently, a wearable electronic device intended to use an electronic device having input/output function, calculation function, and communication function in a state of being very close to or in close contact with a body has been developed. As such a wearable electronic device, devices with an accessory-type shape such as a wristwatch, eyeglasses, and earphones, and a textile-integrated device where electronic functions are incorporated into a garment are known.

An electrical wiring for power supply and signal transmission is necessary for an electronic device. In particular, for a textile-integrated wearable electronic device, the electrical wiring is required to have stretchability in accordance with a stretchable garment. Usually, an electrical wiring composed of a metal wire or metal foil inherently has no practical stretchability, and hence a technique for providing stretching capabilities in a pseudo manner by arranging a metal wire or metal foil in a wave shape or in a repeated horseshoes shape is employed.

In the case of the metal wire, it is possible to form a wiring by regarding the metal wire as an embroidery yarn and sewing it into a garment. However, it is clear that such a method is not suitable for mass production.

A method of forming a wiring by etching the metal foil is common as a method for producing a printed wiring board. A method is known in which the metal foil is attached to a stretchable resin sheet, and a wave-shaped wire is formed in the same manner as in the printed wiring board to make a stretchable wiring in a pseudo manner (Non-Patent Document 1). In this method, a stretchability is given in a pseudo manner by twist deformation of the wave-shaped wiring portion. However, metal foil varies also in the thickness direction due to the twist deformation, and thus if the metal foil is used as a part of a garment, the garment has uncomfortable wearing feeling, which is not preferable. In addition, when the metal foil undergoes excessive deformation due to washing or the like, permanent plastic deformation occurs in the metal foil, and the wiring may have the problem of the durability.

As a method to realize a stretchable conductor wiring, a method using a special conductive paste has been proposed. In such a method, conductive particles such as silver particles, carbon particles, and carbon nanotubes, elastomer such as urethane resin with stretchability, natural rubber, or synthetic rubber, and a solvent etc. are kneaded to form a paste, and using the resulting paste, a wiring is printed and drawn on a garment directly or in combination with a stretchable film substrate or the like.

A conductive composition composed of conductive particles and a stretchable binder resin can macroscopically realize a stretchable conductor. From a microscopic viewpoint, in the conductive composition obtained from the above-mentioned paste, the resin binder portion is deformed upon receiving an external force, and the conductivity is maintained within a range in which the electrical chain of the conductive particles is not broken. The resistivity observed macroscopically is higher than that of metal wires or metal foil. However, since the composition itself has stretchability, the wiring is not required to have a shape like a wave-shaped wiring, and flexibility in the width and the thickness of the wiring increases. Therefore, on a practical level, it is possible to realize a wiring with a low resistance compared with a metal wire.

Patent Document 2 discloses a technique in which silver particles and silicone rubber are combined, and the conductive film on the silicone rubber substrate is further covered with silicone rubber to suppress degradation of conductivity during elongation. Patent Document 3 discloses a combination of silver particles and a polyurethane emulsion and that a conductive film with high conductivity and a high elongation ratio can be obtained. Furthermore, many examples have also been proposed in which improvement of characteristics is attempted by combining conductive particles having a high aspect ratio such as carbon nanotubes, silver fillers, and the like.

Patent Document 4 discloses a technique for directly forming an electrical wiring in a garment by using a printing method.

RELATED ART DOCUMENTS

Patent Documents

Patent Document 1: JP-A-H2-234901
Patent Document 2: JP-A-2007-173226
Patent Document 3: JP-A-2012-54192
Patent Document 4: JP-B-3723565

DISCLOSURE OF THE INVENTION

Problems to be Solved by the Invention

As can be easily inferred from a printed wiring in a general printed wiring board or membrane circuit, an insulating substrate or underlying layer, a patterned conductor layer, and an insulating cover coat layer are required for the electrical wiring. Furthermore, in a wearable electronic device, particularly in a wiring used for such applications of measuring an electric potential of a human body by being worn on the human body, an electrode being in direct contact with the surface of the human body may be required. According to examples of the printed wiring board or the membrane circuit, it is a technical common sense that the surface of such an electrode is plated with a noble metal, tin, solder or the like, or an electrode surface layer that covers the conductor layer with carbon paste containing carbon as a conductive filler or the like is provided.

The underlying layer, the conductor layer, the insulating cover layer, and the electrode surface layer each have a pattern shape unique to itself, and each layer has a thickness required for exhibiting each function. As a result of overlapping each layer, unevenness occurs as a level difference on the surface of the printed wiring. This is the same even in a printed wiring board in which a pattern is formed mainly by the subtractive method and a membrane circuit in which a pattern is formed by the additive method.

FIG. 1 is a schematic view showing a cross section of a conventional printed wiring. An underlying layer 2, a conductor layer 3, an insulation coat layer 4 are formed in this order on a substrate 1 by repeatedly performing a process of printing, drying and curing sequentially, whereby a wiring having the cross-sectional structure as shown in FIG. 1 can be obtained. The part that is not covered with the insulating cover coat and where the conductor layer is exposed is an electrode portion, and the part that is covered with the insulating cover coat is a wiring portion.

FIG. 2 is a schematic view showing a cross section of a case in which an electrode surface layer is provided in a conventional printed wiring. In either case, it can be understood that a level difference is generated at the boundary between the wiring portion and the electrode portion, and unevenness occurs as the level difference on the surface of the printed wiring.

The unevenness as the level difference on the surface of such a printed wiring does not pose a major problem in general electronic devices. However, in a garment-type wearable electronic device, particularly in a wiring that is formed inside the garment and is directly in contact with the surface of a human body, the unevenness may cause discomfort and an uncomfortable feeling while wearing the garment, which may cause impairment of a natural wearing feeling.

Needless to say, as to the above-mentioned impairment of a natural wearing feeling caused by the unevenness as the level difference on the surface of the wiring, the same is true in a stretchable wiring using a metal wiring, and a wiring using an electrically conductive fiber.

On the other hand, particularly for a subject during hard exercising, a subject who works in high temperatures and high humidity environments, and a subject who works in wet environments such as a person who is involved in shipping or fishery, the electrode portion and the wiring portion that are in contact with the surface of the human body have a problem that when the subject perspires, the surface of the electrode and the surface of the wiring portion may stick to the surface of the body with sweat, resulting in a very uncomfortable wearing feeling.

Needless to say, as to the above-mentioned impairment of a wearing feeling in which the surface of the wiring and the surface of the electrode stick to the surface of the body, resulting in an uncomfortable wearing feeling, the same is true in a stretchable wiring using a metal wiring, and a wiring using an electrically conductive fiber.

When an electrical wiring and an electrode are formed using a conductive paste, a screen printing method is generally used. In the screen printing, with a screen plate being in contact with a substrate to be subjected to printing, pattern formation is carried out by transferring an ink or paste to the substrate side through a screen. Since the plate material contacts the substrate to be subjected to printing, in the case where an output composed of a plurality of layers including an underlying layer, a conductor layer, an insulating cover layer, an electrode surface layer, and the like, as required in the present invention, is required, every time one layer is printed, it is necessary to undergo a drying and curing step for that layer. If the substrate is a common rigid substrate, it is necessary to take some countermeasures against thermal shrinkage of the substrate or hysteresis of linear expansion during drying and curing, and dimensional change due to moisture absorption/release caused by heating, etc. However, unless a temperature range at which the substrate is greatly deformed is not used, each layer can be printed in an overlaid manner with almost no problem, and regarding alignment, tolerance can be reduced to such a level that will not cause any problems in engineering by combining with such technique as predicting the dimensional change of the substrate in advance.

However, since a substrate in a garment-type electronic device is a flexible substrate such as a woven fabric, a knitted fabric, a nonwoven fabric, and a stretchable film or a sheet, which are easily deformed by external force, the alignment of layers becomes very difficult. To solve these problems, a method can be used in which a substrate is attached to a temporary fixing base and repeatedly subjected to printing, curing and drying thereon, but it takes time and energy for heating and cooling of an amount corresponding to the heat capacity of the fixing base. In addition, this method is not preferable also from the viewpoint of handling property and the like.

Means for Solving the Problems

The inventors made intensive studies to achieve the above objects, and as a result, found that the main cause of the above-mentioned discomfort is a level difference at the boundary between the electrode surface where the conductor layer or the electrode surface layer is exposed and the wiring portion covered with the insulating cover layer.

Furthermore, the inventors made intensive studies to solve the above problems, and as a result, found that the above-mentioned uncomfortable feeling can be greatly reduced through the shape of the surface of the electrical wiring. In addition, the inventors devised the idea of using a transfer method to solve the above problems and accomplished the following invention.

That is, the present invention has the following constitution.

[1] A garment-type electronic device comprising an electrical wiring comprising a conductor layer, an insulating cover layer, and an insulating underlying layer in a part in contact with a body surface, wherein the electrical wiring has substantially no level difference at a boundary between an electrode portion and a wiring portion.

[2] The garment-type electronic device comprising an electrical wiring according to above [1], wherein the electrical wiring comprises the conductor layer, the insulating cover layer, the insulating underlying layer, and an electrode surface layer.

[3] The garment-type electronic device according to above [1] or [2], wherein the garment-type electronic device can be deformed at a stretching rate of 10% or more without substantially impairing a conductive function of the conductor layer, an insulation function of the insulating cover layer, and an insulation function of the insulating underlying layer.

[4] The garment-type electronic device according to any of above [1] to [3], wherein the conductor layer, the insulating cover layer, and the insulating underlying layer each have an elongation at break of 50% or more and a tensile elastic modulus of 10 to 500 MPa.

[5] A garment-type electronic device comprising an electrical wiring comprising at least a conductor layer, an insulating cover layer, and an insulating underlying layer in a part in contact with a body surface, wherein a surface of a wiring portion of the electrical wiring has projections and depressions in a shape of fabric texture.

[6] The garment-type electronic device comprising an electrical wiring according to above [5], wherein the electrical wiring comprises at least the conductor layer, the insulating cover layer, the insulating underlying layer, and an electrode surface layer.

[7] The garment-type electronic device according to above [5] or [6], wherein, in the projections and the depressions in the shape of fabric texture on the surface of the wiring portion, a repetition pitch of the projections and the depressions is 0.06 mm or more and 12 mm or less on at least one arbitrary straight line.

[8] The garment-type electronic device according to any of above [5] to [7], wherein, in the projections and the depressions in the shape of fabric texture on the surface of the wiring portion, a difference in height between a concave portion and a convex portion is 7 μm or more and 2500 μm or less.

[9] The garment-type electronic device according to any of above [5] to [8], wherein the conductor layer, the insulating cover layer, and the insulating underlying layer each have an elongation at break of 50% or more and a tensile elastic modulus of 10 to 500 MPa.

[10] The garment-type electronic device according to any of above [5] to [9], wherein the garment-type electronic device can be deformed at a stretching rate of 10% or more without substantially impairing a conductive function of the conductor layer, an insulation function of the insulating cover layer, and an insulation function of the insulating underlying layer.

[11] A method for producing a garment-type electronic device comprising an electrical wiring comprising at least a conductor layer, an insulating cover layer, and an insulating underlying layer, the method comprising: preparing the electrical wiring by sequentially printing and stacking the insulating cover layer, the conductor layer, and the insulating underlying layer in this order using an ink or paste-like material on a first substrate exhibiting releasability; and transferring the electrical wiring to a fabric as a second substrate.

[12] A method for producing a garment-type electronic device comprising an electrical wiring comprising at least a conductor layer, an insulating cover layer, an insulating underlying layer, and an electrode surface layer, the method comprising: preparing the electrical wiring by sequentially printing and stacking the insulating cover layer, the electrode surface layer, the conductor layer, and the insulating underlying layer in this order using an ink or paste-like material on a first substrate exhibiting releasability; and transferring the electrical wiring to a fabric as a second substrate.

[13] A method for producing a garment-type electronic device comprising an electrical wiring comprising at least a conductor layer, an insulating cover layer, an insulating underlying layer, and an electrode surface layer, the method comprising: preparing the electrical wiring by sequentially printing and stacking the electrode surface layer, the insulating cover layer, the conductor layer, and the insulating underlying layer in this order using an ink or paste-like material on a first substrate exhibiting releasability; and transferring the electrical wiring to a fabric as a second substrate.

[14] The method for producing a garment-type electronic device according to any of above [11] to [13], wherein the conductor layer, the insulating cover layer, and the insulating underlying layer each have an elongation at break of 50% or more and a tensile elastic modulus of 10 to 500 MPa.

[15] The method for producing a garment-type electronic device according to any of above [11] to [14], wherein the garment-type electronic device can be deformed at a stretching rate of 10% or more without substantially impairing a conductive function of the conductor layer, an insulation function of the insulating cover layer, and an insulation function of the insulating underlying layer.

[16] The method for producing a garment-type electronic device according to any of above [11] to [15], wherein the first substrate exhibiting releasability has projections and depressions in a shape of stripe or in a shape of fabric texture on a surface of the first substrate.

Effects of the Invention

In the electrical wiring used in the garment-type electronic device of the present invention, a level difference at the boundary between the electrode surface where the conductor layer or the electrode surface layer is exposed and the wiring portion covered with the insulating cover layer is substantially eliminated, whereby discomfort during the wearing of the garment-type electronic device is significantly reduced, and hence a natural wearing feeling is realized.

Although a level difference exists also between the wiring portion and the non-wiring portion, the level difference at the boundary between the wiring portion and the non-wiring portion is covered with the underlying layer and the cover layer and thus is gentle. In addition, since both a higher part and a lower part of the level difference are a cover layer composed of the same material, discomfort is small in terms of touch sensation.

However, at the boundary between the electrode portion and the wiring portion, there is an essential difference that each of the electrode portion and the wiring portion is made of a different material. In particular, the electrode portion is composed of a conductor part having electron conductivity such as metal or carbon, which has a high thermal conductivity. On the other hand, the insulating cover layer is composed of an organic material, which has a low thermal conductivity. The inventors made various studies on the shapes of the electrode and the wiring. As a result, the inventors found out that discomfort during the wearing of the garment is caused by the synergistic effect of the level difference between the electrode portion and the insulating cover portion and the difference in thermal conductivity, and that the discomfort during the wearing can be significantly reduced by eliminating the level difference at the boundary.

In addition, in the garment-type electronic device of the present invention in which the level difference at the boundary between the electrode portion and the wiring portion of the electrical wiring is substantially eliminated, since the insulating cover portion is not raised with respect to the electrode portion, not only contact between the electrode and the surface of a human body but also junction with a connector for connection with a discrete component or a module can be smoothly performed.

Improvement of the contact state with the surface of a human body leads to the accuracy of detection of biological signals. Furthermore, in the connector portion, since the outer shape of the connector can fit over the insulating cover portion, it is possible to allow the surface of the electrode not to be exposed. Since an attaching portion has a flat surface without a level difference, it is possible to attach a connector component without forcing the electrode portion to be deformed when attaching, so that an excellent effect of improving the reliability of the connecting portion can be obtained.

In the case where the thickness in the electrical wiring portion varies depending on its parts, when tension is applied to the electrical wiring, the elongation rate of a thicker part is small, and the elongation rate of a thinner part is large, so that the load may locally increase, resulting in shortening the overall material lifetime. In the present invention, since the level difference in the electrical wiring portion is substantially small, such variation in the elongation rate is unlikely to occur, and as a result, the product lifetime can be prolonged.

In the electrical wiring used in the garment-type electronic device of the present invention, by providing projections and depressions in the shape of fabric texture on its surface, the electrical wiring portion is prevented from sticking to the surface of a human body by moistening, and hence an uncomfortable feeling while wearing is reduced.

However, since the formation of the projections and the depressions on the surface of the electrical wiring intuitively reduces the opportunity of contact between the electrode and the surface of the human body, it is concerned that it becomes difficult to detect a signal from the human body. Originally, when a rigid electrode material is used, contact between the flat surface of the electrode and the free curved surface of the human body is intrinsically poor. Practically, the deformation of the human body side allows the contact between the surface of the electrode and the surface of the human body to be generated. A state of giving unnatural deformation to the surface of the body causes a discomfort and is not necessarily a comfortable state.

When the projections and the depressions are formed on the surface of the electrode, if an object under test has a flat surface, the contact area may certainly become small and the detection accuracy may decrease. The inventors have found that, on a flexible surface of a human body, the deformation of the skin follows the projections and the depressions of the surface of the electrode, so that the decrease in the contact area is not as large as it may seem, and the formation of the projections and the depressions on the surface of the electrode in order to reduce an uncomfortable feeling when sweating does not necessarily lead to a reduction in detection accuracy.

Furthermore, in the present invention, by using the electrical wiring composed of flexible materials, the deformation on the human body side and the deformation on the electrode side synergistically act, bringing about a more reliable contact state. More preferably, by using the electrical wiring having stretchability capable of expanding and contracting, the electrode also macroscopically deforms in a free curved surface manner, so that the state of contact between the surface of the electrode and the surface of the human body becomes more reliable.

In addition, due to the provision of the projections and the depressions on the surface, it is concerned that the mechanical strength of the electrical wiring portion may be lowered, and the durability of the garment-type electronic device may be impaired. However, it has been found by the studies of the inventors that even if the projections and the depressions are provided, remarkable deterioration in durability does not occur, and on the contrary, the durability is improved. The inventors consider that the projections and the depressions on the surface substantially provide a bellows structure to the wiring portion, so that flexibility and stretchability are structurally exhibited. The difference in height and the repetition pitch of the projections and the depressions which are preferably provided in the present invention exceed the total thickness of the wiring portion depending on the conditions, and the durability improving effect brought by the bellows structure becomes more remarkable.

Furthermore, in the present invention, by using the electrical wiring composed of flexible materials, the degree of freedom in deformation of the wiring portion is further increased in terms of structure and materials, and by using an electrical wiring having stretchability, the degree of freedom of the wiring portion is further increased, and durability is further improved. In particular, the degree of freedom of deformation in a compression direction is increased, so that improvement in washing durability is expected.

In the production method of the present invention, since layers necessary for the electrical wiring are formed on a releasing intermediate medium having sufficient dimensional stability, the alignment of each of the layers can be performed with high accuracy as compared with the case of directly printing on fabric.

Furthermore, by using the production method of the present invention, it is possible to substantially eliminate a level difference between the electrode portion and the wiring portion. Not only in a garment-type electronic device, but also in general printed wirings, an electrode portion and a wiring leading to an electrode are formed of the same conductive material, an insulating cover layer is formed on the wiring portion, and an electrode surface layer is formed on the electrode portion, so that a level difference is generated at the boundary between the wiring portion and the electrode portion. In the present invention, this level difference can be substantially eliminated, and a discomfort when wearing a garment-type electronic device to be obtained can be significantly reduced. By this action, the garment-type electronic device produced by the production method of the present invention can realize a natural wearing feeling.

In addition, in the garment-type electronic device obtained by the production method of the present invention in which the level difference at the boundary between the electrode portion and the wiring portion of the electrical wiring is substantially eliminated, since the insulating cover portion is not raised with respect to the electrode portion, not only contact between the electrode and the surface of a human body but also junction with a connector for connection with a discrete component or a module can be smoothly performed.

Improvement of the contact state with the surface of a human body leads to the accuracy of detection of biological signals. Furthermore, in the connector portion, since the outer shape of the connector can fit over the insulating cover portion, it is possible to allow the surface of the electrode not to be exposed. Since an attaching portion has a flat surface without a level difference, it is possible to attach a connector component without forcing the electrode portion to be deformed when attaching, so that an excellent effect of improving the reliability of the connecting portion can be obtained.

In the case where the thickness in the electrical wiring portion varies depending on its parts, when tension is applied to the electrical wiring, the elongation rate of a thicker part is small, and the elongation rate of a thinner part is large, so that the load may locally increase, resulting in shortening the overall material lifetime. In the present invention, since the level difference in the electrical wiring portion is substantially small, such variation in the elongation rate is unlikely to occur. In particular, since a steep level difference is eliminated, the local change of the elongation rate can be suppressed, and as a result, the product lifetime can be prolonged.

Furthermore, in the present invention, by forming a predetermined three-dimensional pattern in advance on the surface of the intermediate medium, the pattern can be transferred to the electrical wiring, and hence the electrical wiring having a three-dimensional pattern on the surface can be obtained. By using a fabric shape as a three-dimensional pattern, it is possible to greatly reduce the difference in touch sensation between a part with the wiring and a part without the wiring, whereby improvement in the wearing feeling of the garment-type electronic device can be attained.

BRIEF DESCRIPTION OF THE DRAWINGS

FIG. 1 is a schematic view showing a cross section of a case in which no electrode surface layer is provided in a conventional electrical wiring;

FIG. 2 is a schematic view showing a cross section of a case in which an electrode surface layer is provided in a conventional electrical wiring;

FIG. 3 is a schematic view showing a cross section of a case in which no electrode surface layer is provided in the electrical wiring of the present invention;

FIG. 4 is a schematic view showing a cross section of a case in which an electrode surface layer is provided in the electrical wiring of the present invention;

FIG. 5 is a schematic view showing the process of a production method of a conventional electrical wiring;

FIG. 6 is a schematic view showing an example of the process of a production method of the electrical wiring of the present invention;

FIG. 7 shows an example of the pattern of the electrical wiring of the present invention; and FIG. 8 is a schematic view showing an arrangement position of the example of the electrical wiring of FIG. 7 on a sports shirt.

REFERENCE SIGNS LIST

1. Substrate (fabric)
2. Insulating underlying layer
3. Stretchable conductor composition layer (stretchable conductor layer)
4. Stretchable cover layer (insulating cover layer)
5. Stretchable carbon layer (electrode surface layer)
6. Adhesive layer (insulating underlying layer)
10. Temporary support body (releasing support body)

MODE FOR CARRYING OUT THE INVENTION

Hereinafter, the present invention will be described with reference to the drawings.

FIG. 3 is a schematic view showing a cross section of a case in which no electrode surface layer is provided in the electrical wiring of the present invention. In this example, the conductor layer functions as an electrode as it is. Compared with FIG. 1 showing a cross section of a conventional electrical wiring, the surface of the electrode is flush with the insulating cover layer in the electrical wiring of the present invention, and thus unevenness on the surface of the electrical wiring does not occur.

FIG. 4 is a schematic view showing a cross section of a case in which an electrode surface layer is provided in the electrical wiring of the present invention. Compared with FIG. 2 showing a cross section of a case in which an electrode surface layer is provided in a conventional electrical wiring, the electrode surface layer is flush with the insulating cover layer in the electrical wiring of the present invention, and thus unevenness on the surface of the electrical wiring does not occur.

It is obvious that the electrical wiring in the present invention is flexible. The flexible electrical wiring of the present invention is implemented by forming each of the conductor layer, the insulating cover layer, the insulating underlying layer and the electrode surface layer constituting the electrical wiring from a material having flexibility. Furthermore, the flexible electrical wiring of the present invention is preferably composed of a stretchable material having stretchability, and the electrical wiring preferably has stretchability in addition to flexibility.

Hereinbelow, each layer of the electrical wiring will be explained.

In the present invention, a fabric constituting a part or whole of the garment of the garment-type electronic device can be used as a substrate. Examples of the fabric include a woven fabric, a knitted fabric, and a nonwoven fabric, and coated fabrics obtained by subjecting these fabrics to resin-coating or resin-impregnation and the like can also be used as a substrate. A synthetic rubber sheet typified by Neoprene (registered trademark) can also be used as a substrate. A fabric to be used in the present invention preferably has stretchability capable of repeated stretching of 10% or more. Moreover, the substrate of the present invention preferably has an elongation at break of 50% or more. The substrate of the present invention may be a raw fabric, may be in the form of ribbon or tape, or may be a braid or net, or a piece of fabric cut from a raw fabric.

When the fabric is a woven fabric, examples thereof include plain weave, twill weave, sateen weave, and the like. When the fabric is a knitted fabric, examples thereof include knitted fabrics of plain stitch, modified stitches thereof, moss stitch, crepe stitch, lace stitch, eyelet stitch, plating stitch, pile stitch, rib stitch, ripple stitch, hexagonal stitch, blister stitch, milano rib stitch, double pique stitch, single pique stitch, twill stitch, herringbone stitch, ponte rome stitch, basket stitch, tricot stitch, half tricot stitch, satin tricot stitch, double tricot stitch, queen's cord stitch, striped seersucker stitch, raschel stitch, tulle mesh stitch, modified stitches thereof, and combinations thereof. The fabric may be a nonwoven fabric made of elastomer fiber or the like.

The underlying layer of the present invention has a function of insulation on the substrate side of the wiring portion. Here, the insulation includes mechanical, chemical and biological insulations in addition to electrical insulation, and requires a function to insulate the conductor layer from moisture, chemical substances, biological substances permeating the substrate.

The underlying layer of the present invention is preferably composed of a flexible polymeric material. As the flexible polymer material, a material that is so-called rubber or elastomer can be used. As such rubber or elastomer of the present invention, a resin material for forming a conductor layer described later can be used.

The underlying layer of the present invention preferably has stretchability capable of repeated stretching of 10% or more. In addition, the underlying layer of the present invention preferably has an elongation at break of 50% or more. Furthermore, the underlying layer of the present invention preferably has a tensile elastic modulus of 10 to 500 MPa.

The underlying layer of the present invention is preferably formed by applying a coating liquid, an immersion liquid, a printing ink, a printing paste or the like in a liquid form or a slurry state onto a substrate. To bring a material for the underlying layer into a liquid form or a slurry state, it may be dissolved and dispersed in a solvent. It is within the scope of the present invention to blend a known leveling agents, thixotropic property imparting agent, and the like for adjusting printability and the like. The solvent is appropriately selected from solvents and the like which can be used for a conductive paste described later.

In the present invention, as a special case, when a precursor of a material for forming the underlying layer is a liquid, it is also possible that a layer formed using the precursor is subjected to an appropriate reaction to form an underlying layer.

When it is difficult to bring a material for forming the underlying layer of the present invention into in a liquid state or a slurry state, the material can be processed into a film form or a sheet form by melt extrusion molding or press molding and attached to a substrate with an adhesive or the like. Alternatively, the material can be processed into a film or sheet in a precursor state, and then solidified by a predetermined reaction to obtain a film or sheet.

The conductor layer of the present invention refers to a layer composed of a material having a specific resistance of $1 \times 10^0$ Ωcm or less. The conductor layer of the present invention preferably has stretchability. The stretchability in the present invention means that stretching of 10% or more can be repeatedly performed. As for the conductor layer of the present invention, the elongation at break of the conductor layer alone is preferably 50% or more. Furthermore, the conductor layer of the present invention preferably has a tensile elastic modulus of 10 to 500 MPa. A material having such stretchability is called a stretchable conductor composition.

The stretchable conductor composition can be obtained from a conductive paste described below. Hereinafter, a conductive paste as one of implementation means for the components of the present invention will be explained. The conductive paste is composed of at least conductive particles, nonconductive particles to be preferably added, a stretchable resin, and a solvent.

The conductive particles of the present invention are composed of a material having a specific resistance of $1 \times 10^{-1}$ Ωcm or less and have a particle diameter of 100 μm or less. Examples of the material having a specific resistance of $1 \times 10^{-1}$ Ωcm or less include metal, alloy, carbon, doped semiconductor, conductive polymer, and the like. As the conductive particles preferably used in the present invention, metals such as silver, gold, platinum, palladium, copper, nickel, aluminum, zinc, lead, and tin, alloy particles such as brass, bronze, cupronickel, and solder, hybrid particles such as silver-coated copper, metal-plated polymer particles, metal-plated glass particles, metal-coated ceramic particles, and the like can be used.

In the present invention, it is preferred to mainly use flaky silver particles or an irregular-shaped aggregated silver powder. Here, the "mainly use" means that the amount of 90% by mass or more of the conductive particles is used. The irregular-shaped aggregated powder is made by three-dimensional aggregation of spherical or irregular-shaped primary particles. The irregular-shaped aggregated powder and the flaky powder are preferable because they have a specific surface area larger than that of spherical powder or the like, and hence an electrical conductivity network can be formed even when the filling amount is small. The irregular-shaped aggregated powder, which is not in a monodisperse form, is further preferable because the particles physically contact with each other, and hence an electrical conductivity network can be easily formed.

Although there is no particular limitation for the particle diameter of the flaky powder, the average particle diameter (50% D) measured by a dynamic light scattering method is preferably 0.5 to 20 μm, and more preferably 3 to 12 μm. If the average particle diameter exceeds 15 μm, the formation of a fine wiring may become difficult, and clogging occurs in the case of screen printing or the like. If the average particle diameter is less than 0.5 μm, the particles cannot contact with each other when the filling amount is small, and as a result, the electrical conductivity may deteriorate.

Although there is no particular limitation for the particle diameter of the irregular-shaped aggregated powder, the average particle diameter (50% D) measured by a light scattering method is preferably 1 to 20 μm, and more preferably 3 to 12 μm. If the average particle diameter exceeds 20 μm, the dispersibility decrease, and as a result, paste formation may become difficult. If the average particle diameter is less than 1 μm, the effects as the aggregated powder is lost, and as a result, high electrical conductivity may not be maintained when the filling amount is small.

The nonconductive particles in the present invention are composed of an organic or inorganic insulating material. The inorganic particles in the present invention are added for the purpose of improving printing properties, stretching properties and coating film surface properties, and inorganic particles such as silica, titanium oxide, talc, and alumina, microgel made of a resin material, and the like can be used.

In the present invention, it is preferable to use barium sulfate particles as non-conductive particles. As the barium sulfate particles in the present invention, ground barite obtainable by grinding a barite mineral called a natural barite, and a so-called precipitated barium sulfate produced by a chemical reaction can be used. It is preferred in the present invention to use the precipitated barium sulfate of which particle diameter is easily controlled. The average particle diameter of the barium sulfate particles preferably used, as determined by a dynamic light scattering method, is preferably 0.01 to 18 μm, more preferably 0.05 to 8 μm, and further preferably 0.2 to 3 μm. In addition, the barium sulfate particles in the present invention are preferably subjected to a surface treatment with a hydroxide and/or oxide of one or both of Al and Si. By such a surface treatment, the hydroxide and/or oxide of one or both of Al and Si adhere to the surface of the barium sulfate particles. The adhering amount of these compounds is preferably 0.5 to 50, and more preferably 2 to 30 relative to 100 of barium elements at an element ratio detected by X-ray fluorescence analysis.

The average particle diameter of the barium sulfate particles is preferably smaller than the average particle diameter of the conductive particles. The number average particle diameter of the conductive particles is preferably 1.5 times or more, further preferably 2.4 times or more, and still further preferably 4.5 times or more of the number average particle diameter of the barium sulfate particles. When the average particle diameter of the barium sulfate particles exceeds the above range, the irregularities on the surface of the resulting coat increase, which tends to cause a fracture of the coat when stretched. On the other hand, when the average particle diameter of the barium sulfate particles is smaller than the above range, the stretching durability enhancement effect is insufficient, the viscosity of the paste is increased, and as a result, it becomes difficult to manufacture the paste.

The barium sulfate particles in the present invention is contained in an amount of 2 to 30% by mass, preferably 3 to 20% by mass, and more preferably 4 to 15% by mass relative to the total amount of the conductive particles and the barium sulfate particles. If the amount of the barium sulfate particles exceeds the above range, the electrical conductivity of the surface of the resulting coat lowers. On the other hand, if the amount of the barium sulfate particles is less than the above range, the stretching durability enhancement effect tends to be hardly developed.

It is preferred to use a flexible resin as the resin in the present invention. As the flexible resin in the present invention, thermoplastic resins, thermosetting resins, or rubbers having an elastic modulus of 1 to 1000 MPa can be given. In order to develop the film stretchability, rubbers are preferable. Examples of the rubbers include urethane rubber, acrylic rubber, silicone rubber, butadiene rubber, rubber containing a nitrile group such as nitrile rubber or hydrogenated nitrile rubber, isoprene rubber, vulcanized rubber, styrene-butadiene rubber, butyl rubber, chlorosulfonated polyethylene rubber, ethylene propylene rubber, vinylidene fluoride copolymer, and the like. Among these, rubber containing a nitrile group, chloroprene rubber, and chlorosulfonated polyethylene rubber are preferable, and rubber containing a nitrile group is particularly preferable. The elastic modulus in the present invention is preferably within a range of 3 to 600 MPa, more preferably 10 to 500 MPa, further preferably 30 to 300 MPa.

There is no particular limitation for the rubber containing a nitrile group as far as it is a rubber or elastomer containing a nitrile group, and nitrile rubber and hydrogenated nitrile rubber are preferable. Nitrile rubber is a copolymer of butadiene with acrylonitrile, and when the amount of bonding acrylonitrile increases, affinity with metal increases but rubber elasticity contributing to stretchability rather decreases. Therefore, the amount of bonding acrylonitrile in the acrylonitrile butadiene copolymer rubber is preferably 18 to 50% by mass, and more preferably 40 to 50% by mass.

The flexible resin in the present invention is contained in an amount of 7 to 35% by mass, preferably 9 to 28% by mass, and more preferably 12 to 20% by mass relative to the total amount of the conductive particles, the nonconductive particles to be preferably added, and the flexible resin.

Furthermore, an epoxy resin may be blended to the conductive paste in the present invention. The epoxy resin in the present invention is preferably a bisphenol A type epoxy resin or a phenol novolac type epoxy resin. When blending an epoxy resin, a curing agent for the epoxy resin may be blended. As the curing agent, known amine compounds, polyamine compounds and the like can be used. The curing agent is preferably contained in an amount of 5 to 50% by mass, and more preferably 10 to 30% by mass relative to the epoxy resin. Moreover, the amount of the epoxy resin and the curing agent is 3 to 40% by mass, preferably 5 to 30% by mass, more preferably 8 to 24% by mass relative to the all resin components including the flexible resin.

The present invention contains a solvent. The solvent in the present invention is water or an organic solvent. The content of the solvent is not particularly limited since it should be appropriately investigated depending on the viscosity required of the paste, and it is generally preferred to be 30 to 80 in a mass ratio when the total mass of the conductive particles, the barium sulfate particles and the flexible resin is defined as 100.

As to the organic solvent used in the present invention, its boiling point is preferred to be equal to or higher than 100° C. and lower than 300° C., and more preferred to be equal to or higher than 130° C. and lower than 280° C. When the boiling point of the organic solvent is too low, the solvent may be evaporated during the paste production process and during use of the paste, and there is concern that the ratio of the ingredients constituting the conductive paste will be apt to change. On the other hand, when the boiling point of the organic solvent is too high, the amount of solvent remaining in the dried and cured coat becomes large, and hence there is concern that reliability of the coat will deteriorate.

Specific examples of the organic solvent using in the present invention include cyclohexanone, toluene, xylene, isophorone, γ-butyrolactone, benzyl alcohol, Solvesso 100, 150 and 200 (manufactured by Exxon Chemical), propylene glycol monomethyl ether acetate, terpineol, butyl glycol acetate, diamylbenzene, triamylbenzene, n-dodecanol, diethylene glycol, ethylene glycol monoethyl ether acetate, diethylene glycol monoethyl ether acetate, diethylene glycol monobutyl ether acetate, diethylene glycol dibutyl ether, diethylene glycol monoacetate, triethylene glycol diacetate, triethylene glycol, triethylene glycol monomethyl ether, triethylene glycol monoethyl ether, triethylene glycol monobutyl ether, tetraethylene glycol, tetraethylene glycol monobutyl ether, tripropylene glycol, tripropylene glycol monomethyl ether, and 2,2,4-trimethyl-1,3-pentanediol monoisobutyrate. As to a petroleum hydrocarbon, there may be exemplified AF Solvent No. 4 (boiling point: 240 to 265° C.), No. 5 (boiling point: 275 to 306° C.), No. 6 (boiling point: 296 to 317° C.), No. 7 (boiling point: 259 to 282° C.), and No. 0 Solvent H (boiling point: 245 to 265° C.) etc. manufactured by Nippon Oil Corporation. If necessary, the organic solvent may be used singly, or in combination of two or more thereof. Such organic solvents are appropriately contained such that a conductive silver paste has a viscosity suitable for printing or the like.

The paste for forming a stretchable conductor in the present invention can be prepared by mixing and dispersing the conductive particles, the barium sulfate particles, the stretchable resin, and the solvent as materials with a disperser such as a dissolver, three-roll mill, rotation/revolution mixer, attritor, ball mill, sand mill or the like.

Into the paste for forming a stretchable conductor in the present invention, a known organic or inorganic additive such as a printability imparting agent, color tone adjusting agent, leveling agent, antioxidant, ultraviolet absorber, or the like can be blended as long as the contents of the invention are not impaired.

The insulating cover layer of the present invention has a function of insulation on the surface side of the wiring portion. Here, the insulation includes mechanical, chemical and biological insulations in addition to electrical insulation, and requires a function to insulate the conductor layer from moisture, chemical substances, biological substances permeating the substrate.

The insulating cover layer of the present invention is preferably composed of a flexible polymeric material. As the flexible polymer material, a material that is so-called rubber or elastomer can be used. As such rubber or elastomer of the present invention, a resin material for forming the conductor layer can be used.

The insulating cover layer of the present invention preferably has stretchability capable of repeated stretching of 10% or more. In addition, the insulating cover layer of the present invention preferably has an elongation at break of 50% or more. Furthermore, the insulating cover layer of the present invention preferably has a tensile elastic modulus of 10 to 500 MPa.

The insulating cover layer of the present invention is preferably formed by applying a coating liquid, an immersion liquid, a printing ink, a printing paste or the like in a liquid form or a slurry state onto a substrate. To bring a material for the insulating cover layer into a liquid form or a slurry state, it may be dissolved and dispersed in a solvent. It is within the scope of the present invention to blend a known leveling agents, thixotropic property imparting agent and the like for adjusting printability and the like. The solvent is appropriately selected from solvents and the like which can be used for a conductive paste.

In the present invention, as a special case, when a precursor of a material for forming an insulating cover layer is a liquid, it is also possible that a layer formed using the precursor is subjected to an appropriate reaction to form an insulating cover layer. The case where an ultraviolet curable resin or the like is used falls under this case.

When it is difficult to bring a material for forming the insulating cover layer of the present invention into in a liquid state or a slurry state, it is also possible that the material is processed into a film form or sheet form, for example, by melt extrusion molding or press molding, and then the film or sheet is processed into an appropriate outer shape and attached to a substrate with an adhesive or the like.

The electrode surface layer in the present invention literally means a layer to be used when coating the surface of the electrode with a material different from the wiring portion. As the electrode surface layer, noble metal plating such as gold plating, platinum plating, and rhodium plating, solder plating, tin plating or the like can be used.

The electrode surface layer of the present invention preferably has stretchability capable of repeated stretching of 10% or more. In addition, the electrode surface layer of the present invention preferably has an elongation at break of 50% or more. Furthermore, the electrode surface layer of the present invention preferably has a tensile elastic modulus of 10 to 500 MPa.

When stretchability is required also for the electrode portion as described above, it is possible to form the electrode surface layer using a stretchable carbon paste. The carbon paste in the present invention can be regarded as a carbon paste in which the conductive particles in the conductive paste for forming the conductor layer are limited to conductive carbon. However, with respect to the blending amount of the conductive particles, since the carbon particles have a specific gravity smaller than that of metal and a specific surface area larger than that of metal, it is preferred to blend the conductive particles in an amount of about one-half to one-eighth of the mass % of a metal powder. Other conditions, dispersion method and the like for obtaining the carbon paste, are the same as those for the conductive paste.

In the present invention, that "the electrical wiring has substantially no level difference at a boundary between an electrode portion and a wiring portion" means that the thicker portion and the thinner portion of the wiring do not have a distinct boundary therebetween, and in a transition region where a change in level difference of at least 50 μm occurs, the thickness varies within the transition region of the width of 1.0 mm or more, preferably 2.0 mm or more, more preferably 3.0 mm or more. Such thickness variation of the boundary portion may be determined from a profile determined with a non-contact-type thickness meter. More specifically, using a wide double-sided tape, the wiring portion together with the fabric that is a substrate is attached to a flat plate in a state in which tension is applied in a surface direction to such an extent that a distinct slack does not occur to prepare a sample, and the profile of the sample may be determined by an optical thickness meter. If the level difference at the boundary is within the above-mentioned range, the existence of a level difference is not felt when touched, and therefore it can be said that the electrical wiring has substantially no level difference.

It is preferred that the wiring portion of the garment-type electronic device of the present invention can be deformed at a stretching rate of 10% or more without substantially impairing the conductive function of the conductor layer, the insulation function of the insulating cover layer, and the insulation function of the insulating underlying layer. More specifically, the wiring portion of the garment-type electronic device is cut out, and the conductive functions and the insulation functions before and after stretching the wiring portion at a stretching rate of 10% with a tensile tester can be compared. The conductive function is evaluated by the resistance value of the wiring, and if the resistance value in a state where the wiring is stretched at a stretching rate of 10% is equal to or smaller than 100 times the resistance value at a stretching rate of 0%, the conductive function is evaluated to be maintained. In a state where the insulating underlying layer is stretched at a stretching rate of 10% and then the stretching rate is returned to 0%, unless separation of the insulating underlying layer from the substrate occurs, the insulation function is determined to be maintained. With respect to the insulating cover layer, unless cracks that can be visually recognized occur in a state of a stretching rate of 10%, the insulation function is determined to be maintained.

The conductor layer, the insulating cover layer, and the insulating underlying layer of the present invention each preferably have an elongation at break of 50% or more, and a tensile elastic modulus of 10 to 500 MPa. The elongation at break and the tensile elastic modulus of each layer can be determined by applying a paste material constituting each layer onto a release sheet to form a film with a prescribed thickness, separating the film after drying, and subjecting it to a tensile test.

In the present invention, the projections and the depressions in the shape of fabric texture can be provided on the surface of the wiring portion of the electrical wiring. The shape of fabric texture in the present invention means a shape in which a difference in height exists according to a specific rule in the Z axis direction on the X-Y two-dimensional plane, and preferably refers to a shape having a regular repetition in at least two directions (that do not necessarily have to be orthogonal) on the X-Y plane. Although the repetition period may be random, it is necessary to satisfy at least the average repetition pitch defined in the present invention. The shape of fabric texture preferably used in the present invention is a shape made by literally transferring a shape of an actual fabric, or by imitating the repeated pattern of a fabric or the repeated pattern of a knitted fabric. The shape of fabric texture may be of either fabric texture with regularity of woven fabric or knitted fabric, or fabric texture with unclear regularity of nonwoven fabric. When the fabric is a woven fabric, examples thereof include plain weave, twill weave, sateen weave, and the like. When the fabric is a knitted fabric, examples thereof include knitted fabrics of plain stitch, modified stitches thereof, moss stitch, crepe stitch, lace stitch, eyelet stitch, plating stitch, pile stitch, rib stitch, ripple stitch, hexagonal stitch, blister stitch, milano rib stitch, double pique stitch, single pique stitch, twill stitch, herringbone stitch, ponte rome stitch, basket stitch, tricot stitch, half tricot stitch, satin tricot stitch, double tricot stitch, queen's cord stitch, striped seersucker stitch, raschel stitch, tulle mesh stitch, modified stitches thereof, and combinations thereof. The fabric may be a nonwoven fabric made of elastomer fiber or the like.

In the projections and the depressions in the shape of fabric texture on the surface of the wiring portion as described above, when the fabric texture has regularity, it is preferred that the repetition pitch of the projections and the depressions be 0.2 mm or more and 12 mm or less on an arbitrary straight line drawn on the surface of the wiring. The repetition pitch is preferably in the range of 0.5 mm or more and 9 mm or less, more preferably 1.0 mm or more and 8 mm or less, further preferably 1.6 mm or more and 7 mm or less, and still further preferably 2.4 mm or more and 6 mm or less. If the repetition pitch is outside the predetermined range, the effect on touch sensation becomes unsatisfactory.

In the projections and the depressions in the shape of fabric texture of the present invention, the difference in height between a concave portion and a convex portion is preferably 7 µm or more and 2500 µm or less. The difference in height is more preferably 15 µm or more and 1500 µm or less, further preferably 25 µm or more and 900 µm or less, still further preferably 48 µm or more and 600 µm or less. If the difference in height between a concave portion and a convex portion is outside the predetermined range, the effect on touch sensation becomes unsatisfactory.

The projections and the depressions of the surface of the electrical wiring portion as described above may be determined from a profile determined with a noncontact-type thickness meter. More specifically, using a wide double-sided tape, the wiring portion together with the fabric that is a substrate is attached to a flat plate in a state in which tension is applied in a surface direction to such an extent that a distinct slack does not occur and used as a sample, and the profile of the sample may be determined by an optical thickness meter. If the level difference at the boundary is within the above-mentioned range, the existence of a level difference is not felt when touched, and therefore it can be said that the electrical wiring has substantially no level difference. In the present invention, it is preferable to use a three-dimensional measuring function of a laser microscope as the optical thickness meter.

A means for realizing the electrical wiring having substantially no level difference at the boundary between the electrode portion and the wiring portion in the present invention will be described. In the present invention, a portion where the conductor layer is exposed is an electrode portion, and a portion covered with the insulating cover layer is a wiring portion.

As a means for realizing the electrical wiring having no level difference of the present invention, a method of stacking an extremely thin insulating cover layer on a conductor layer can be exemplified. If the thickness of the conductor layer is 50 µm or more and the thickness of the insulating cover layer is less than 10 µm, the level difference is not tactually felt, and hence it can be regarded that the electrical wiring has substantially no level difference.

As a means for realizing the electrical wiring having no level difference of the present invention, a method can be exemplified in which an underlying layer, a conductor layer, an insulating cover layer, and if necessary, an electrode surface layer are sequentially stacked on a substrate by printing, dried and cured, and then subjected to a pressure molding at a temperature equal to or higher than the softening temperature of each layer. Since this method needs processing at relatively high temperatures, an applicable substrate may be limited in some cases.

In the present invention, it is possible to obtain an electrical wiring having substantially no level difference by using a transfer method described below.

In the transfer method in the present invention, a predetermined wiring pattern, insulating pattern and the like are printed on an intermediate medium to form an electrode surface layer, an insulating cover layer, a conductor layer, and an underlying layer in this order, and then transferred to a fabric as a substrate, whereby an electrical wiring can be obtained. When the ease of transfer is further desired, a hot-melt layer as an underlying layer can be formed on the wiring pattern printed on the intermediate medium in advance, and then a transfer to a fabric can be performed. Furthermore, the hot-melt layer may be provided as an image receiving layer on the fabric side in advance. For such a hot-melt layer, a thermoplastic urethane resin or the same flexible resin used for the binder component of the stretchable conductor composition of the present invention can be used.

As the intermediate medium in this case, a so-called release sheet such as a polymer film or paper having a release layer on its surface may be used. In addition, it is possible to use a film, sheet, plate or the like having a surface made of a material poor in adhesiveness such as fluororesins, silicone resins, or polyimides. It is also possible to use a metal plate such as stainless steel, a hard chrome-plated steel plate, an aluminum plate or the like.

In the present invention, as a means for realizing the electrical wiring having the projections and the depressions in the shape of fabric texture on its surface, a method can be exemplified in which an underlying layer, a conductor layer, an insulating cover layer, and if necessary, an electrode surface layer are sequentially stacked by printing on a substrate, and in drying or after drying and curing, embossing is performed at a temperature equal to or higher than the softening temperature of each layer. As an embossing method, press work of pushing an embossing mold against a layer and an emboss roller method of pushing an embossing roller against a layer can be exemplified. These methods can be preferably used when the repetition pitch is relatively wide, i.e., 3 mm or more, preferably 2 mm or more. These methods are also preferably applicable when a difference in height between the projections and the depressions is relatively large, i.e., 300 µm or more, preferably 600 µm or more. Since these methods need processing at relatively high temperatures, an applicable substrate may be limited in some cases.

In the present invention, it is possible to easily obtain an electrical wiring having projections and depressions in the shape of fabric texture on its surface by forming a reversed pattern of the projections and the depressions in the shape of fabric texture in advance on the intermediate medium in the transfer method.

In the present invention, the intermediate medium on which the reversed pattern of the projections and the depressions in the shape of fabric texture is formed in advance can be produced by embossing if a thermoplastic film is used as the intermediate medium. When a plate material of metal, resin or the like is used, a predetermined fabric texture may be read with a three-dimensional scanner, and the plate material may be cut in the shape of the fabric texture with a three-dimensional processing machine. The intermediate medium may be produced using a 3D printer, which is being practically used recently.

In the present invention, in order to produce an intermediate medium on which the reversed pattern of the projections and the depressions in the shape of fabric texture is formed in a laboratory manner, for example, a fabric having a shape of fabric texture to be desired to use is affixed to a plate material, a release agent is applied to the surface of the fabric with a spray or the like, and silicone resin for molding is applied to the entire surface and peeled off after being cured, whereby a mold transfer intermediate medium which the reversed pattern of the shape of fabric texture to be desired to use is formed on its surface can be obtained.

EXAMPLES

Hereinafter, the invention will be explained in more detail and specifically by further showing examples. Evaluation results etc. of examples were measured by the following method.

<Amount of Nitrile>

The amount of nitrile was converted from the composition ratio obtained by analyzing the resulting resin material by NMR to a ratio by mass (% by mass) of monomer.

<Mooney Viscosity>

The measurement was conducted using SMV-300RT "Mooney Viscometer" manufactured by Shimadzu Corporation.

<Average Particle Diameter>

The measurement was performed using a light-scattering particle size distribution analyzer LB-500 manufactured by Horiba, Ltd.

<Elastic Modulus and Elongation at Break>

Each material was applied to a release sheet so as to have a dry thickness of 100±10 μm, followed by drying and curing under predetermined conditions, and the resulting sheet together with the release sheet were punched out into a dumbbell shape defined by ISO 527-2-1A to obtain a test piece. At the time of measurement, the sheet of each material was peeled off from the release sheet and subjected to a tensile test by the method defined in ISO 527-1 to determine an elastic modulus and an elongation at break.

<Stretching Characteristics of Electrical Wiring Portion>

The electrical wiring portion excluding the electrode portion of the produced garment-type electronic device was cut out such that the straight line part of the wiring was 100 mm in length to obtain a test piece. After visually confirming that the wiring portion was not peeled off from the fabric that was a substrate, and no crack or the like occurred on the surface of the insulating cover layer in the test piece, the insulating cover layer at the end of the wiring was scraped off to allow the resistance value of the wiring to be measured, and the wiring was connected to a terminal of a resistance measuring instrument. The clip was set in a tensile tester subjected to an electrical insulation treatment so that a portion to be stretched had an effective length of 50 mm, and an initial resistance value, a resistance value when stretched at a predetermined elongation rate, and a wiring resistance value when returned to the initial state were measured.

The initial resistance value was referred to as R0, a resistance value at 10% stretching was referred to as R10, and a resistance change rate Rv=R10/R0 was determined. A case where Rv≤100 was considered that the conductive function was maintained, and thus evaluated as "good", and a case where Rv>100 was considered that the conductive function was lost, and thus evaluated as "poor". A case where cracks visually confirmed on the insulating cover layer of the electrical wiring did not occur after the test was considered that the insulation function was maintained, and thus evaluated as "good", and a case where cracks occurred was considered that the insulation function was lost, and thus evaluated as "poor". Furthermore, a case where no peeling of the underlying layer from the substrate occurred after the test was considered that the insulation function was maintained, and thus evaluated as "good", and a case where the peeling occurred was considered that the insulation function was lost, and thus evaluated as "poor".

The procedure in which the test piece was stretched by 10%, kept for one second, then returned to the initial state and held for one second was repeatedly performed 100 times, and then the same evaluation was carried out.

<Measurement of Resistance of Wiring>

The resistance value of the wiring was measured using Milliohmmeter manufactured by Agilent Technologies.

<Level Difference>

A portion including the electrode portion and the wiring portion was cut out into a rectangle of 50 mm×100 mm from the garment-type electronic device to obtain a test piece. The test piece was attached using a double-sided tape having a width of 50 mm such that the wiring portion having a thickness of 10 mm together with the fabric that was the substrate did not slacken, and then, a thickness profile from the electrode portion to the wiring portion was determined with an optical thickness meter.

As for the absolute value of the slope of 10 mm of from 5 mm on the electrode side to 5 mm on the wiring side at the boundary between the electrode portion and the wiring portion, a case where a ratio of level difference/measurement length (10 mm) was less than 50/3000 was evaluated as "very good", a case where the ratio was 50/3000 or more and less than 50/2000 was evaluated as "good", a case where the ratio was 50/2000 or more and less than 50/1000 was evaluated as "fair", and a case where the ratio was 50/1000 or more was evaluated as "poor".

<Wearing Feeling>

Ten adult men as test subjects wore the garment provided with an electrical wiring which was produced in the Examples and did the radio exercise No. 1 and the radio exercise No. 2 successively while measuring an electrocardiogram. With regard to the wearing feeling during that time, the sensory evaluation was performed according to 5 grades from 5 points as "good feeling" to 1 point as "bad feeling". Averaging points of ten subjects, a case of 4 points or more was evaluated as "very good", a case of 3 points or more and less than 4 points was evaluated as "good", a case of 2 points or more and less than 3 points was evaluated as "fair", and a case of less than 2 points was evaluated as "poor".

<Difference in Height and Repetition Pitch of Projections and Depressions in the Shape of Fabric Texture>

A portion including the electrode portion and the wiring portion was cut out into a rectangle of 50 mm×100 mm from the garment-type electronic device to obtain a test piece. The test piece was attached using a double-sided tape having a width of 50 mm such that a wiring portion having a thickness of 10 mm together with the fabric that was the substrate did not slacken, and then, the test piece was observed with a laser microscope VK-X200 manufactured by Keyence Corporation, the obtained data was subjected to data processing with an analysis application for VK-X100/X200, and the difference in height between the projections and the depressions was determined. The difference in height was measured for 5 concave portions and the average thereof was taken. Subsequently, a ruler with a scale of 0.5 mm was placed on the test piece so as to be in a random direction, and the repetition pitch of the projections and the depressions was measured. In the measurement, the average of the pitch intervals for 10 repetitions was firstly determined, the same operation was performed 5 times in total in other directions randomly selected, and the average value of the determined 5 average values was further determined and taken as a repetition pitch.

<Wearing Feeling>

Ten adult men as test subjects wore the garment provided with an electrical wiring which was produced in the Examples and ran a half-marathon while measuring an electrocardiogram. With regard to the wearing feeling during that time, the sensory evaluation was performed according to 5 grades from 5 points as "good feeling" to 1 point as "bad feeling". Averaging points of ten subjects, a case of 4 points or more was evaluated as "very good", a case of 3 points or more and less than 4 points was evaluated as "good", a case of 2 points or more and less than 3 points was evaluated as "fair", and a case of less than 2 points was evaluated as "poor".

<Washing Durability>

The garment was put in a square-shaped laundry net of 40 cm×50 cm, and using a spin-dryer-equipped household washing machine having a standard washing volume and a standard water volume which meets the standard of JIS C 9606 (electric washing machine) as specified in the washing method 103 of JIS L 0217 "Labeling Marks for Handling of Textile Products and Labeling Methods Thereof", the garment was washed for 15 minutes without using a detergent, dewatered for 10 minutes, taken out, and dried in the shade indoors. Then, the electrical continuity of the wiring portion of the garment was checked, and a case where the electrical continuity was confirmed was evaluated as "good", and a case where the electrical continuity was broken or unstable was evaluated as "poor".

<Misalignment>

Using trim marks for alignment provided on each layer in advance, a positional gap between the conductor layer and the insulating cover layer was measured with a length measuring machine capable of measuring in units of μm. The trim marks were provided in the portions corresponding to the four corners of the necessary print pattern so as to align with a rectangular screen plate used for printing. The screen plate was set so as to align with at least one of the trim marks when printing, printing was carried out, a vector amount was determined from the amount of positional gap in the X-Y direction at each of the four corners, and the average value of the absolute values of the vector amounts at the four points was determined.

Production Example

<Polymerization of Synthetic Rubber Material>

The following materials were put into a stainless steel reactor equipped with a stirrer and a water cooling jacket and gently stirred while keeping the bath temperature at 15° C. by flowing nitrogen.

| | |
|---|---|
| butadiene | 54 parts by mass |
| acrylonitrile | 46 parts by mass |
| deionized water | 270 parts by mass |
| sodium dodecylbenzenesulfonate | 0.5 part by mass |
| sodium naphthalenesulfonate condensate | 2.5 parts by mass |
| t-dodecyl mercaptan | 0.3 part by mass |
| triethanolamine | 0.2 part by mass |
| sodium carbonate | 0.1 part by mass |

Next, an aqueous solution prepared by dissolving 0.3 part by mass of potassium persulfate in 19.7 parts by mass of deionized water was added dropwise into the reactor over 30 minutes, reaction was further continued for 20 hours, an aqueous solution prepared by dissolving 0.5 part by mass of hydroquinone in 19.5 parts by mass of deionized water was then added thereto, and an operation for stopping the polymerization reaction was carried out.

Next, in order to distill off unreacted monomers, the pressure in the reactor was first reduced, and then steam was introduced into the reactor to recover the unreacted monomers, thereby to obtain a synthetic rubber latex (L1) composed of NBR. Sodium chloride and dilute sulfuric acid were added to the obtained latex, aggregation and filtration were performed. Then, deionized water in an amount 20 times in volume ratio to the resin was divided in five portions, the resin was washed by repeating redispersion in the deionized water and filtration, and dried in air to obtain a synthetic rubber resin R1.

The evaluation results of the obtained synthetic rubber resin R1 are shown in Table 1. Then, the operations were similarly performed by changing raw materials, polymerization conditions, washing conditions, and the like to obtain resin materials R2 to R4 shown in Table 1. Abbreviations in the table are as follows:

NBR: acrylonitrile butadiene rubber

NBIR: acrylonitrile-isoprene rubber (isoprene: 10% by mass)

SBR: styrene-butadiene rubber (styrene/butadiene=50/50% by mass)

TABLE 1

| latex | L1 | L2 | L3 | L4 |
|---|---|---|---|---|
| stretchable resin | R1 | R2 | R3 | R4 |
| component | NBR | NBR | NBIR | SBR |
| polymerization temperature | 15 | 12 | 15 | 20 |
| Amount of nitrile [mass %] | 43 | 35 | 26 | 0 |
| Mooney viscosity | 53 | 42 | 34 | 64 |

Production Example 1.5 parts by mass of a liquid bisphenol-A based epoxy resin with an epoxy equivalent of 175 to 195, 10 parts by mass of the stretchable resin (R1) obtained in the production example, and 0.5 part by mass of the latent curing agent [trade name: Amicure PN23 manufactured by Ajinomoto Fine Chemical Co., Ltd.] were mixed and stirred with 30 parts by mass of isophorone to be dissolved, thereby to obtain a binder resin composition A1. Next, 58.0 parts by mass of fine flaky silver powder [trade name: Ag-XF301 manufactured by Fukuda Metal Foil & Powder Co., Ltd.] having an average particle diameter of 6 μm was added to the binder resin composition A1, uniformly mixed and dispersed by a three-roll mill to obtain a conductive paste AG1. The evaluation results of the obtained conductive paste AG1 are shown in Table 2a and Table 2b.

Then, blending was carried out by changing the materials to obtain conductive pastes AG2 to AG6 as shown in Table 2a and Table 2b. Likewise, the evaluation results are shown in Table 2a and Table 2b.

Note that in Tables 2a and 2b, amorphous silver powder 1 is an aggregated silver powder G-35 (average particle diameter: 6.0 μm) manufactured by DOWA Electronics, and amorphous silver powder 2 is an aggregated silver powder having an average particle diameter of 2.1 μm obtained by wet-classifying the aggregated silver powder G-35 manufactured by DOWA Electronics.

Then, in the same manner as in the production of the conductive paste, the formulation was changed in accordance with Table 2a and Table 2b to obtain a carbon paste CB1 for the electrode surface layer, and pastes CC1 and CC2 for the underlying layer and the insulating cover layer. The evaluation results are shown in Table 2a and Table 2b. The pastes CC1 and CC2 not containing solid particles was obtained by dissolving the resin component in a solvent.

TABLE 2a

| blending material | | | Production Example 1 AG1 | Production Example 2 AG2 | Production Example 3 AG3 | Production Example 4 AG4 | Production Example 5 AG5 | Production Example 6 CB1 | Production Example 7 CC1 |
|---|---|---|---|---|---|---|---|---|---|
| Vehicle | epoxy resin | parts by mass | 1.5 | — | — | — | — | — | — |
| | stretchable resin (R1) | parts by mass | 10.0 | — | — | — | 12.0 | — | 30.0 |
| | stretchable resin (R2) | parts by mass | — | 12.0 | — | — | — | 25.0 | — |
| | stretchable resin (R3) | parts by mass | — | — | 12.0 | — | — | — | — |
| | stretchable resin (R4) | parts by mass | — | — | — | 12.0 | — | — | — |
| | curing agent | parts by mass | 0.5 | — | — | — | — | — | — |
| | isophorone | parts by mass | 30.0 | 30.0 | 30.0 | 30.0 | 30.0 | 80.0 | 40.0 |
| Solid particle | scaly silver powder | parts by mass | 58.0 | — | — | — | — | — | — |
| | amorphous silver powder 1 | parts by mass | — | 58.0 | 58.0 | — | 52.0 | — | — |
| | amorphous silver powder 2 | parts by mass | — | — | — | 58.0 | — | — | — |
| | graphite BF | parts by mass | — | — | — | — | — | 12.0 | — |
| | ketchen black | parts by mass | — | — | — | — | — | 2.0 | — |
| | barium sulfate A | parts by mass | — | — | — | — | 6.0 | — | — |
| | specific resistance | Ωcm | $1.8 \times 10^{-4}$ | $2.3 \times 10^{-4}$ | $2.0 \times 10^{-4}$ | $5.0 \times 10^{-4}$ | $3.5 \times 10^{-4}$ | $3.0 \times 10^{-1}$ | — |
| | elastic modulus | MPa | 250 | 120 | 90 | 120 | 180 | 360 | 60 |
| | elongation at break | % | 75 | 210 | 190 | 180 | 160 | 90 | 240 |

TABLE 2b

| blending material | | | Production Example 8 CC2 | Production Example 9 AG6 | Production Example 12 AG12 | Production Example 15 AG15 | Production Example 22 AG22 | Production Example 23 AG23 |
|---|---|---|---|---|---|---|---|---|
| Vehicle | epoxy resin | parts by mass | 14.0 | 5.5 | — | — | — | — |
| | stretchable resin (R1) | parts by mass | 15.0 | 6.0 | 6.0 | 12.0 | 6.0 | — |
| | stretchable resin (R2) | parts by mass | — | — | 6.0 | — | 6.0 | — |
| | stretchable resin (R3) | parts by mass | — | — | — | — | — | 8.0 |
| | stretchable resin (R4) | parts by mass | — | — | — | — | — | 4.0 |
| | curing agent | parts by mass | 1.0 | 0.5 | — | — | — | — |
| | isophorone | parts by mass | 40.0 | 30.0 | 30.0 | 30.0 | 30.0 | 30.0 |
| Solid particle | scaly silver powder | parts by mass | — | 58.0 | — | — | 10.0 | — |
| | amorphous silver powder 1 | parts by mass | — | — | 58.0 | 22.0 | 40.0 | 38.0 |
| | amorphous silver powder 2 | parts by mass | — | — | — | 30.0 | 8.0 | 20.0 |
| | graphite BF | parts by mass | — | — | — | — | — | — |
| | ketchen black | parts by mass | — | — | — | — | — | — |
| | barium sulfate A | parts by mass | — | — | — | 6.0 | — | — |
| | specific resistance | Ωcm | — | $1.2 \times 10^{-4}$ | $2.3 \times 10^{-4}$ | $3.0 \times 10^{-4}$ | $1.4 \times 10^{-4}$ | $1.8 \times 10^{-4}$ |
| | elastic modulus | MPa | 1300 | 2200 | 120 | 180 | 95 | 68 |
| | elongation at break | % | 45 | 30 | 210 | 170 | 170 | 220 |

Example 1

A garment-type electronic device for measuring an electrocardiogram was produced by the transfer method as shown in FIG. 6.

On a release PET film having a thickness of 125 μm, first, the carbon paste CB1 for forming an electrode surface layer was screen-printed in a predetermined pattern and then dried and cured, and subsequently, the insulating paste CC1 for forming an insulating cover layer was screen-printed in a predetermined pattern, and then dried and cured. The electrode surface layer for measuring an electrocardiogram was a circle with a diameter of 30 mm. The insulating cover layer had a doughnut shape having an inner diameter of 30 mm and an outer diameter of 36 mm at the electrode portion, and the wiring portion extending from the electrode had a width of 14 mm. A circular electrode with a diameter of 10 mm was similarly printed with a carbon paste at the end of the wiring portion in order to attach a hook for connection to a sensor. The dry film thicknesses of the carbon paste layer and the insulating cover layer were 25 μm and 15 μm, respectively.

Next, an electrode portion and a wiring portion were screen-printed using the silver paste AG1 for forming a conductor layer, and dried and cured under predetermined conditions. The electrode portion was a circle having a diameter of 32 mm, the wiring portion had a width of 10 mm, and the dry thickness of these portions on the insulating cover layer was adjusted to be 30 μm. An underlying layer was further screen-printed using the same CC1 used for the insulating cover layer and dried so as to have a dry thickness of 20 μm. Furthermore, another underlying layer was printed under the same conditions and dried such that the solvent remained in an amount of 25% by mass by adjusting the drying time to leave the surface tackiness, whereby a transferable printed electrical wiring was obtained.

Next, the transferable printed electrical wiring obtained by the above process was overlaid on a predetermined portion of a sports shirt turned inside out which was made of knitted fabric, and pressed at room temperature to temporarily bond the printed electrical wiring to the back side of the sports shirt. Then, the release PET film was peeled off, and the sports shirt was hung on a hanger and dried at 115° C. for 30 minutes to obtain a sports shirt provided with an electrical wiring. The wiring pattern is shown in FIG. 7, and the arrangement of the wiring pattern on the shirt is shown in FIG. 8.

In the obtained sports shirt provided with the electrical wiring, the circular electrode having a diameter 30 mm was placed on the intersection of each of left and right posterior axillary lines and the seventh rib, and the electrical wiring composed of the stretchable conductor having a width of 10 mm extending from each of the circular electrodes to the center of the posterior neck was formed on the inside of the sports shirt. The wirings extending from the left and right electrodes to the center of the posterior neck had a gap of 5 mm therebetween at the center of the neck, and both wirings were not short-circuited.

Subsequently, a stainless steel hook was attached on the outer side at the center edge of the posterior neck, and in order to ensure electrical continuity with the wiring portion on the inner side, the stainless steel hook was electrically connected to the stretchable conductor composition layer using a conductive yarn in which a fine metal wire was twisted.

Heart rate sensor WHS-2 manufactured by Union Tool Co. was connected via the stainless steel hook, and was programmed so that a heart rate data could be received and displayed with a smartphone manufactured by Apple in which the application "myBeat" designed specifically for the heart rate sensor WHS-2 had been installed. In this way, the sports shirt in which a heart rate measurement function was incorporated was produced.

This shirt was worn by a subject, the subject did the radio exercise No. 1 and the radio exercise No. 2 successively, and the electrocardiogram data of the subject during these exercises was acquired. The acquired electrocardiogram data had less noise and a high resolution, and hence had a quality as an electrocardiogram that is capable of analyzing mental states, physical condition, fatigue, sleepiness, stress levels, or the like from the change in heart rate interval, the electrocardiogram waveform, and the like. The same shirt was worn by ten subjects, and the feeling of wearing was evaluated. The results are shown in Table 3 and Table 4.

A predetermined test piece was cut out from a sports shirt produced under the same conditions as in the sports shirt used in the wearing test. For the test piece, the level difference at the boundary between the electrode portion and the wiring portion was evaluated, and the maintenance performances of the electrical conductivity of the wiring, the insulating property of the insulating cover layer, and the insulating property of the underlying layer were evaluated on each case where 10% stretching was carried out once and 100 times. The results are shown in Table 3 and Table 4.

Then, sports shirts of Examples 2 to 6 and Comparative Examples 1 to 2 were produced in the same manner as above according to the configurations as shown in Table 3 and Table 4, and evaluated in the same manner as above. The results are shown in Table 3 and Table 4.

Comparative Examples 3 to 5

The sports shirt made of knitted fabric used in Example 1 was turned inside out, put in a frame so that wrinkles did not form on the back side, and fixed by pinning both shoulders and left and right hems of the shirt.

Next, a sports shirt having the same wiring pattern as that of the Examples was produced by the direct printing method as shown in FIG. 5. First, an underlying layer was screen-printed with the CC paste in a predetermined pattern, dried under predetermined conditions, further printed again under the same conditions, and dried and cured. Next, a conductor layer, an insulating cover layer, and an electrode surface layer were each printed and dried in this order to obtain an electrical wiring. A hook was attached to the obtained sports shirt, and a heart rate sensor WHS-2 manufactured by Union Tool Co. was connected in the same manner as in the Examples, and the evaluation was carried out in the same manner as in the Examples. The results are shown in Table 3 and Table 4.

In Comparative Example 1, a break in electrical continuity in the wiring portion occurred at the first wearing, and it was impossible to acquire electrocardiogram data. In Comparative Example 2, initial electrocardiogram data could be acquired without problems, but noise increased in course of doing the radio exercise, and it became impossible to acquire data in the middle of the radio exercise No. 2. In Comparative Examples 3 to 5, it was possible to acquire data to the end, but in Comparative Example 5 in which the initial specific resistance was relatively high, in the test of repeatedly stretching 100 times, the resistance value on stretching was more than 100-fold the initial resistance value, and the evaluation was "poor".

TABLE 3

| | | Example 1 electrical wiring 1 | Example 2 electrical wiring 2 | Example 3 electrical wiring 3 | Example 4 electrical wiring 4 | Example 5 electrical wiring 5 | Example 6 electrical wiring 6 |
|---|---|---|---|---|---|---|---|
| Wiring configuration | electrode surface layer | CB1 | CB1 | CB1 | CB1 | CB1 | none |
| | insulating cover layer | CC1 | CC1 | CC1 | CC1 | CC1 | CC1 |
| | conductor layer | AG1 | AG2 | AG3 | AG4 | AG5 | AG5 |
| | underlying layer | CC1 | CC1 | CC1 | CC1 | CC1 | CC1 |
| | substrate | knitted fabric | knitted fabric | knitted fabric | knitted fabric | knitted fabric | knitted fabric |
| Wiring formation method | | transfer | transfer | transfer | transfer | transfer | transfer |
| level difference | | good | good | good | good | good | good |
| wearing feeling | | good | good | good | good | good | good |
| stretching once | maintenance performance of conductivity | good | good | good | good | good | good |
| | insulating property of the insulating cover layer | good | good | good | good | good | good |
| | insulating property of the underlying layer | good | good | good | good | good | good |
| stretching 100 times | maintenance performance of conductivity | good | good | good | good | good | good |
| | insulating property of the insulating cover layer | good | good | good | good | good | good |
| | insulating property of the underlying layer | good | good | good | good | good | good |

TABLE 4

|  |  | Comparative Example 1 electrical wiring 7 | Comparative Example 2 electrical wiring 8 | Comparative Example3 electrical wiring 8 | Comparative Example 4 electrical wiring 8 | Comparative Example5 electrical wiring 8 |
|---|---|---|---|---|---|---|
| Wiring configuration | electrode surface layer | CB1 | CB1 | CB1 | CB1 | CB1 |
|  | insulating cover layer | CC1 | CC2 | CC1 | CC1 | CC1 |
|  | conductor layer | AG6 | AG2 | AG2 | AG3 | AG4 |
|  | underlying layer | CC1 | CC1 | CC1 | CC1 | CC1 |
|  | substrate | knitted fabric | knitted fabric | knitted fabric | knitted fabric | knitted fabric |
| Wiring formation method |  | transfer | transfer | direct printing | direct printing | direct printing |
| level difference |  | good | good | poor | poor | poor |
| wearing feeling |  | poor | poor | poor | poor | poor |
| stretching once | maintenance performance of conductivity | poor | good | good | good | good |
|  | insulating property of the insulating cover layer | good | poor | good | good | good |
|  | insulating property of the underlying layer | good | poor | good | good | good |
| stretching 100 times | maintenance performance of conductivity | poor | good | good | good | poor |
|  | insulating property of the insulating cover layer | good | poor | good | good | good |
|  | insulating property of the underlying layer | poor | poor | good | good | good |

Production Example 1 of Releasing Intermediate Medium

A plain woven stainless steel screen of 500 mesh was attached, with a double-sided adhesive tape, to a basswood plywood sheet having a thickness of 12 mm which was provided with a dam with a height of 15 mm at the periphery of the sheet, and a PVA adhesive as a releasing agent was applied to the screen in an amount necessary to allow half of the screen in the thickness direction to be buried during drying, dried by air-drying for 20 hours, and further dried in a dry oven at 70° C. for 2 hours. Next, a two-component curable type silicone resin was poured into the screen so as to have a thickness of about 5 mm, and cured at room temperature over 24 hours. After curing, the silicone resin was peeled off to obtain a transfer mold 1 having the projections and the depressions of a plain weave pattern.

Then, using the stainless steel screens and polyester screens of different meshes, the operation was conducted in the same manner as above to obtain transfer molds as shown in Table 5.

Production Example 2 of Releasing Intermediate Medium

A tricot woven fabric was attached, with a double-sided adhesive tape, to a basswood plywood sheet having a thickness of 12 mm which was provided with a dam with a height of 15 mm at the periphery of the sheet, and a PVA adhesive as a releasing agent and fluff inhibitor was applied to the screen so as to fully penetrate the fabric, dried by air-drying for 20 hours, and further dried in a dry oven at 70° C. for 2 hours. Next, a two-component curable type silicone resin was poured into the fabric so as to have a thickness of about 5 mm, and cured at room temperature over 24 hours. After curing, the silicone resin was peeled off to obtain a transfer mold having the projections and the depressions of a tricot stitch knitted fabric.

Using another fabric, the operation was conducted in the same manner as above to obtain a transfer mold as shown in Table 5.

<Production Example of Embossing Mold>

A part of the plain woven screen used in the production example of the releasing intermediate medium was read with a 3D scanner and processed into digital data. After reversing the negative/positive of the projections and the depressions in the form of the digital data, the repetition pitch and the difference in height of the projections and the depressions were deformed so as to have predetermined values, followed by molding with a 3D printer. Next, a releasing agent was applied to the obtained molded product, then five glass cloths impregnated with an epoxy resin that is cured at room temperature were stacked thereon, the whole was placed in a thick futon compression bag, and the bag was decompressed by a vacuum cleaner. The whole was taken out after 24 hours, and the cured FRP part was removed. Then, the back side of the cured FRP was filled with thermosetting putty and flattened to obtain an embossing mold.

Then, molding was carried out in the same manner as above by changing the repetition pitch and the difference in height of the projections and the depressions, thereby to obtain embossing molds as shown in Table 5.

TABLE 5

| mold | shape of fabric texture | repetition pitch of the projections and the depressions mm | Difference in height of projections and depressions μm |
|---|---|---|---|
| transfer mold 1 | plain woven 400 mesh | 0.063 | 12 |
| transfer mold 2 | plain woven 300 mesh | 0.082 | 16 |
| transfer mold 3 | plain woven 130 mesh | 0.16 | 28 |
| transfer mold 4 | plain woven 70 mesh | 0.35 | 62 |
| transfer mold 5 | tricot A | 2.4 | 140 |
| transfer mold 6 | tricot B | 3.8 | 220 |
| embossing mold 1 | plain woven 200 mesh | 0.12 | 37 |
| embossing mold 2 | plain woven 50 mesh | 0.5 | 70 |
| embossing mold 3 | plain woven 25 mesh | 1.0 | 280 |
| embossing mold 4 | plain woven 8 mesh | 3.1 | 950 |
| embossing mold 5 | plain woven 4 mesh | 6.2 | 2100 |
| embossing mold 6 | plain woven 1.5 mesh | 16.7 | 2800 |
| embossing mold 7 | plain woven 12.5 mesh | 2.0 | 5 |
| embossing mold 8 | plain woven 12.5 mesh | 2.0 | 21 |
| embossing mold 9 | plain woven 12.5 mesh | 2.0 | 350 |
| embossing mold 10 | plain woven 12.5 mesh | 2.0 | 3500 |

<Examples and Comparative Example According to a Transfer Method>

Examples 101 to 120 and Comparative Examples 101 to 108

A garment-type electronic device for measuring an electrocardiogram was produced by the transfer method as shown in FIG. 6.

First, the carbon paste CB1 for forming an electrode surface layer was screen-printed in a predetermined pattern on the transfer mold 4 as shown in Table 5, and then dried and cured. Subsequently, the insulating paste CC1 for forming an insulating cover layer was screen-printed in a predetermined pattern, and then dried and cured. The electrode surface layer for measuring an electrocardiogram was a circle with a diameter of 30 mm. The insulating cover layer had a doughnut shape having an inner diameter of 30 mm and an outer diameter of 36 mm at the electrode portion, and the wiring portion extending from the electrode had a width of 14 mm. A circular electrode with a diameter of 10 mm was similarly printed with a carbon paste at the end of the wiring portion in order to attach a hook for connection to a sensor. The dry film thicknesses of the carbon paste layer and the insulating cover layer were 25 μm and 30 μm, respectively.

Next, an electrode portion and a wiring portion were screen-printed using the silver paste AG1 for forming a conductor layer, and dried and cured under predetermined conditions. The electrode portion was a circle having a diameter of 32 mm, the wiring portion had a width of 10 mm, and the dry thickness of these portions on the insulating cover layer was adjusted to be 40 μm. An underlying layer was further screen-printed using the same CC1 used for the insulating cover layer and dried so as to have a dry thickness of 40 μm. Furthermore, another underlying layer was again printed under the same conditions, and dried such that the solvent remained in an amount of 25% by mass by adjusting the drying time to leave the surface tackiness, whereby a transferable printed electrical wiring was obtained.

Next, the transferable printed electrical wiring obtained by the above process was overlaid on a predetermined portion of a sports shirt turned inside out which was made of knitted fabric, and pressed at room temperature to temporarily bond the printed electrical wiring to the back side of the sports shirt. Then, the transfer mold was peeled off, and the sports shirt was hung on a hanger and further dried at 115° C. for 30 minutes to obtain a sports shirt provided with an electrical wiring having a pattern in a plain weave form on the surface.

In the obtained sports shirt provided with the electrical wiring, the circular electrode having a diameter 30 mm was placed on the intersection of each of left and right posterior axillary lines and the seventh rib, and the electrical wiring composed of the stretchable conductor having a width of 10 mm extending from each of the circular electrodes to the center of the posterior neck was formed on the inside of the sports shirt. The wirings extending from the left and right electrodes to the center of the posterior neck had a gap of 5 mm therebetween at the center of the neck, and both wirings were not short-circuited.

Subsequently, a stainless steel hook was attached on the outer side at the center edge of the posterior neck, and in order to ensure electrical continuity with the wiring portion on the inner side, the stainless steel hook was electrically connected to the stretchable conductor composition layer using a conductive yarn in which a fine metal wire was twisted.

Heart rate sensor WHS-2 manufactured by Union Tool Co. was connected via the stainless steel hook, and was programmed so that a heart rate data could be received and displayed with a smartphone manufactured by Apple in which the application "myBeat" designed specifically for the heart rate sensor WHS-2 had been installed. In this way, the sports shirt in which a heart rate measurement function was incorporated was produced. The wiring pattern is shown in FIG. 7, and the arrangement of the wiring pattern on the shirt is shown in FIG. 8.

This shirt was worn by a subject, the subject ran a half-marathon distance, and the electrocardiogram data of the subject during this running was acquired. The acquired electrocardiogram data had less noise and a high resolution, and hence had a quality as an electrocardiogram that is capable of analyzing mental states, physical condition, fatigue, sleepiness, stress levels, or the like from the change in heart rate interval, the electrocardiogram waveform, and the like. The same shirt was worn by ten subjects, and the feeling of wearing was evaluated. The results are shown in Tables 6a, 6b and 6c.

A predetermined test piece was cut out from a sports shirt produced under the same conditions as in the sports shirt used in the wearing test. For the test piece, the level difference at the boundary between the electrode portion and the wiring portion was evaluated, and the maintenance performances of the electrical conductivity of the wiring, the insulating property of the insulating cover layer, and the insulating property of the underlying layer were evaluated on each case where 10% stretching was carried out once and 100 times. The results are shown in Tables 6a, 6b, 6c, 7a, 7b and 7c.

Then, sports shirts were produced in the same manner as above according to the configurations as shown in Tables 6a, 6b, 6c, 7a, 7b and 7c, and evaluated in the same manner as above. The results are shown in Tables 6a, 6b, 6c, 7a, 7b and 7c.

<Examples and Comparative Examples According to a Direct Printing Method+Embossing>

A garment-type electronic device for measuring an electrocardiogram was produced by the direct printing method as shown in FIG. 5.

The sports shirt made of knitted fabric used in Example 101 was turned inside out, put in a frame so that wrinkles did not form on the back side, and fixed by pinning both shoulders and left and right hems of the shirt.

Next, a sports shirt having the same wiring pattern as that of the Examples was produced by the direct printing method as shown in FIG. 5. First, an underlying layer was screen-printed with the CC paste in a predetermined pattern, dried under predetermined conditions, further printed again under the same conditions, and dried and cured. Next, a conductor layer, an insulating cover layer, and an electrode surface layer in this order were each printed and dried to obtain an electrical wiring.

<Embossing>

The obtained shirt provided with the electrical wiring was placed on a silicone rubber sheet having a thickness of 3 mm with the wiring surface facing upward, the embossing mold 4 as shown in Table 5 was stacked thereon, and they were placed on a hot plate heated to 90° C. and pressed to transfer the projections and the depressions of the embossing mold to the wiring surface.

A hook was attached to the sports shirt subjected to embossing, and a heart rate sensor WHS-2 manufactured by Union Tool Co. was connected in the same manner as in the Examples to obtain a sports shirt in which a heart rate measurement function was incorporated. Then, the evaluation was carried out in the same manner as in the Examples. The results are shown in Tables 6a, 6b, 6c, 7a, 7b and 7c.

<Examples and Comparative Examples According to a Transfer Method+Embossing>

An electrical wiring was formed by the transfer method as shown in FIG. 6 using a release PET film instead of the transfer mold and then subjected to embossing using a predetermined embossing mold, thereby to produce a garment-type electronic device for measuring an electrocardiogram. The evaluation was carried out in the same manner as above. The results are shown in Tables 6a, 6b, 6c, 7a, 7b and 7c.

In the rows of use mold in Tables 6a, 6b, 6c, 7a, 7b, and 7c, the examples in which both the release PET and the embossing mold are indicated are examples of a combination of the transfer method and the embossing.

Comparative Example 1, which is a case where a conductor layer with poor flexibility was used, has no problem in wearing feeling but poor durability against stretching. Comparative Examples 102 and 104, which are cases where the wiring surface was not subjected to processing into a shape of fabric texture, has a problem with wearing feeling. Particularly in exercises involving much perspiration such as long-distance running, it can be construed that the flat wiring surface sticks to the skin and an uncomfortable feeling increases. Comparative Example 103, which is an example of a conductor layer having poor flexibility, has a problem in stretching durability. Although Example 110 has some problems in stretching durability, the wearing feeling and the washing durability are improved, and it can be seen that the durability against stretching is somewhat improved in the case of providing the projections and the depressions. In Comparative Example 105, a surface pattern of a so-called high mesh plain woven fabric was used, but the repetition pitch and the difference in height of the projections and the depressions are both too small to have an effect of improving wearing feeling. On the contrary, Comparative Example 106, which is a case where the repetition pitch and the difference in height of the projections and the depressions are too large, has a poor effect of improving wearing feeling and further has a slight problem in stretching durability. Comparative Example 107, which is a case where the difference in height of the projections and the depressions is small, has a poor effect of improving wearing feeling. On the contrary, Comparative Example 108 is a case where the difference in height of the projections and the depressions is large. It can be construed that if the projections and the depressions formed by embossing are too large, a break in electrical continuity in the conductor layer is likely to occur.

TABLE 6a

| | | | Example101 | Example102 | Example103 | Example104 | Example105 |
|---|---|---|---|---|---|---|---|
| Wiring configuration | electrode surface layer | | CB1 | CB1 | CB1 | CB1 | CB1 |
| | insulating cover layer | | CC1 | CC1 | CC1 | CC1 | CC1 |
| | conductor layer | | AG1 | AG12 | AG3 | AG4 | AG15 |
| | underlying layer | | CC1 | CC1 | CC1 | CC1 | CC1 |
| | substrate | | knitted fabric | knitted fabric | knitted fabric | knitted fabric | knitted fabric |
| Wiring formation method | | | transfer | transfer | transfer | transfer | transfer |
| use mold | | | transfer mold 4 | transfer mold 4 | transfer mold 4 | transfer mold 4 | transfer mold 4 |
| shape | fabric texture | shape | plain woven 70 mesh | plain woven 70 mesh | plain woven 70 mesh | plain woven 70 mesh | plain woven 70 mesh |
| | pitch | mm | 0.35 | 0.35 | 0.35 | 0.35 | 0.35 |
| | difference in height | μm | 38 | 40 | 37 | 36 | 37 |
| wearing feeling | | | very good | very good | very good | very good | very good |
| stretching once | maintenance performance of conductivity | | good | good | good | good | good |
| | insulating property of the insulating cover layer | | good | good | good | good | good |
| | insulating property of the underlying layer | | good | good | good | good | good |
| stretching 100 times | maintenance performance of conductivity | | good | good | good | good | good |
| | insulating property of the insulating cover layer | | good | good | good | good | good |
| | insulating property of the underlying layer | | good | good | good | good | good |
| Washing durability | | | good | good | good | good | good |

TABLE 6b

| | | | Example106 | Comparative Example 101 | Comparative Example 102 | Example107 | Example108 |
|---|---|---|---|---|---|---|---|
| Wiring configuration | electrode surface layer | | none | CB1 | CB1 | CB1 | CB1 |
| | insulating cover layer | | CC1 | CC1 | CC1 | CC2 | CC1 |
| | conductor layer | | AG15 | AG6 | AG12 | AG12 | AG12 |
| | underlying layer | | CC1 | CC1 | CC1 | CC1 | CC1 |
| | substrate | | knitted fabric | knitted fabric | knitted fabric | knitted fabric | knitted fabric |
| Wiring formation method | | | transfer | transfer | direct printing | direct printing | direct printing |
| use mold | | | transfer mold 4 | transfer mold 4 | none | embossing mold 4 | embossing mold 4 |
| shape | fabric texture | shape | plain woven 70 mesh | plain woven 70 mesh | flat | plain woven 8 mesh | plain woven 8 mesh |
| | pitch | mm | 0.35 | 0.35 | — | 3.1 | 3.1 |
| | difference in height | μm | 41 | 41 | — | 620 | 580 |

TABLE 6b-continued

|  |  | Example106 | Comparative Example 101 | Comparative Example 102 | Example107 | Example108 |
|---|---|---|---|---|---|---|
| wearing feeling |  | very good | good | poor | poor | very good |
| stretching once | maintenance performance of conductivity | good | poor | good | good | good |
|  | insulating property of the insulating cover layer | good | good | good | good | good |
|  | insulating property of the underlying layer | good | good | good | good | good |
| stretching 100 times | maintenance performance of conductivity | good | — | good | good | good |
|  | insulating property of the insulating cover layer | good | — | good | good | good |
|  | insulating property of the underlying layer | good | — | good | good | good |
| Washing durability |  | good | poor | good | good | good |

TABLE 6c

|  |  |  | Example109 | Comparative Example 103 | Example110 | Comparative Example 104 |
|---|---|---|---|---|---|---|
| Wiring configuration | electrode surface layer |  | CB1 | CB1 | CB1 | CB1 |
|  | insulating cover layer |  | CC1 | CC1 | CC1 | CC1 |
|  | conductor layer |  | AG15 | AG6 | AG6 | AG15 |
|  | underlying layer |  | CC1 | CC1 | CC1 | CC1 |
|  | substrate |  | knitted fabric | knitted fabric | knitted fabric | knitted fabric |
| Wiring formation method |  |  | direct printing | direct printing | direct printing | transfer |
| use mold |  |  | embossing mold 4 | releasing PET | embossing mold 4 | releasing PET |
| shape | fabric texture | shape | plain woven 8 mesh | flat | plain woven 8 mesh | flat |
|  | pitch | mm | 3.1 | — | 3.1 | — |
|  | difference in height | μm | 570 | — | 600 | — |
| wearing feeling |  |  | very good | poor | very good | poor |
| stretching once | maintenance performance of conductivity |  | good | poor | good | good |
|  | insulating property of the insulating cover layer |  | good | good | good | good |
|  | insulating property of the underlying layer |  | good | good | good | good |
| stretching 100 times | maintenance performance of conductivity |  | good | — | poor | good |
|  | insulating property of the insulating cover layer |  | good | — | good | good |
|  | insulating property of the underlying layer |  | good | — | good | good |
| Washing durability |  |  | good | good | good | good |

TABLE 7a

|  |  |  | Comparative Example105 | Example111 | Example112 | Example113 | Example114 |
|---|---|---|---|---|---|---|---|
| Wiring configuration | electrode surface layer |  | CB1 | CB1 | CB1 | CB1 | CB1 |
|  | insulating cover layer |  | CC1 | CC1 | CC1 | CC1 | CC1 |
|  | conductor layer |  | AG15 | AG15 | AG15 | AG15 | AG15 |
|  | underlying layer |  | CC1 | CC1 | CC1 | CC1 | CC1 |
|  | substrate |  | knitted fabric | knitted fabric | knitted fabric | knitted fabric | knitted fabric |
| Wiring formation method |  |  | transfer | transfer | transfer | transfer | transfer |
| use mold |  |  | transfer mold 1 | transfer mold 2 | transfer mold 3 | transfer mold 5 | transfer mold 6 |
| shape | fabric texture | shape | plain woven 500 mesh | plain woven 400 mesh | plain woven 130 mesh | tricot A | tricot B |
|  | pitch | mm | 0.063 | 0.082 | 0.12 | 2.3 | 3.8 |
|  | difference in height | μm | 4 | 9 | 17 | 90 | 220 |
| wearing feeling |  |  | poor | good | good | very good | very good |
| stretching once | maintenance performance of conductivity |  | good | good | good | good | good |
|  | insulating property of the insulating cover layer |  | good | good | good | good | good |
|  | insulating property of the underlying layer |  | good | good | good | good | good |

TABLE 7a-continued

|  |  | Comparative Example105 | Example111 | Example112 | Example113 | Example114 |
|---|---|---|---|---|---|---|
| stretching 100 times | maintenance performance of conductivity | good | good | good | good | good |
|  | insulating property of the insulating cover layer | good | good | good | good | good |
|  | insulating property of the underlying layer | good | good | good | good | good |
| Washing durability |  | good | good | good | good | good |

TABLE 7b

|  |  |  | Example115 | Example116 | Example117 | Example118 | Comparative Example106 |
|---|---|---|---|---|---|---|---|
| Wiring configuration | electrode surface layer |  | CB1 | CB1 | CB1 | CB1 | CB1 |
|  | insulating cover layer |  | CC1 | CC1 | CC1 | CC1 | CC1 |
|  | conductor layer |  | AG15 | AG15 | AG15 | AG15 | AG15 |
|  | underlying layer |  | CC1 | CC1 | CC1 | CC1 | CC1 |
|  | substrate |  | knitted fabric | knitted fabric | knitted fabric | knitted fabric | knitted fabric |
| Wiring formation method |  |  | transfer | transfer | transfer | transfer | transfer |
| use mold |  |  | releasing PET/ embossing mold 1 | releasing PET/ embossing mold 2 | releasing PET/ embossing mold 3 | releasing PET/ embossing mold 5 | releasing PET/ embossing mold 6 |
| shape | fabric texture | shape | plain woven 200 mesh | plain woven 50 mesh | plain woven 25 mesh | plain woven 4 mesh | plain woven 1.5 mesh |
|  | pitch | mm | 0.12 | 0.5 | 1.0 | 6.2 | 16.7 |
|  | difference in height | μm | 21 | 45 | 180 | 1300 | 2700 |
| wearing feeling |  |  | good | very good | very good | very good | poor |
| stretching once | maintenance performance of conductivity |  | good | good | good | good | good |
|  | insulating property of the insulating cover layer |  | good | good | good | good | good |
|  | insulating property of the underlying layer |  | good | good | good | good | good |
| stretching 100 times | maintenance performance of conductivity |  | good | good | good | good | poor |
|  | insulating property of the insulating cover layer |  | good | good | good | good | good |
|  | insulating property of the underlying layer |  | good | good | good | good | good |
| Washing durability |  |  | good | good | good | good | good |

TABLE 7c

|  |  |  | Comparative Example107 | Example119 | Example120 | Comparative Example108 |
|---|---|---|---|---|---|---|
| Wiring configuration | electrode surface layer |  | CB1 | CB1 | CB1 | CB1 |
|  | insulating cover layer |  | CC1 | CC1 | CC1 | CC1 |
|  | conductor layer |  | AG15 | AG15 | AG15 | AG15 |
|  | underlying layer |  | CC1 | CC1 | CC1 | CC1 |
|  | substrate |  | knitted fabric | knitted fabric | knitted fabric | knitted fabric |
| Wiring formation method |  |  | transfer | transfer | transfer | transfer |
| use mold |  |  | releasing PET/ embossing mold 7 | releasing PET/ embossing mold 8 | releasing PET/ embossing mold 9 | releasing PET/ embossing mold 10 |
| shape | fabric texture | shape | plain woven 12.5 mesh | plain woven 12.5 mesh | plain woven 12.5 mesh | plain woven 12.5 mesh |
|  | pitch | mm | 2.0 | 2.0 | 2.0 | 2.0 |
|  | difference in height | μm | 3 | 16 | 210 | 2900 |
| wearing feeling |  |  | poor | fair | good | good |
| stretching once | maintenance performance of conductivity |  | good | good | good | poor |
|  | insulating property of the insulating cover layer |  | good | good | good | good |
|  | insulating property of the underlying layer |  | good | good | good | good |
| stretching 100 times | maintenance performance of conductivity |  | good | good | good | — |
|  | insulating property of the insulating cover layer |  | good | good | good | — |
|  | insulating property of the underlying layer |  | good | good | good | — |
| Washing durability |  |  | good | good | good | poor |

<Production Example Using a Releasing Intermediate Medium Having the Projections and the Depressions in the Shape of Fabric Texture>

Examples 201 to 205

A plain woven stainless steel screen of 150 mesh was attached, with a double-sided adhesive tape, to a basswood plywood sheet having a thickness of 12 mm which was provided with a dam with a height of 15 mm at the periphery of the sheet, and a PVA adhesive as a releasing agent was applied to the screen in an amount necessary to allow half of the screen in the thickness direction to be buried during drying, dried by air-drying for 20 hours, and further dried in a dry oven at 70° C. for 2 hours. Next, a two-component curable type silicone resin was poured into the screen so as to have a thickness of about 5 mm, and cured at room temperature over 24 hours. After curing, the silicone resin was peeled off to obtain a transfer mold having the projections and the depressions of a plain weave pattern.

Using the obtained transfer mold in place of the release PET film of Example 1, electrical wirings were produced according to the configurations as shown in Table 8 and evaluated in the same manner as above. The results are shown in Table 8.

<Production Example Using a Releasing Intermediate Medium Having Stripe-Like Projections and Depressions>

Using a 3D printer, a releasing intermediate medium having stripe-like projections and depressions was produced. The stripes had a pitch of 2 mm, the repetition of the projections and the depressions was formed as a sinusoidal wave having an amplitude of 50 μm.

Using the obtained transfer mold having the stripe-like projections and depressions in place of the release PET film of Example 1, an electrical wiring was produced according to the configurations as shown in Table 8 and evaluated in the same manner as above. The results are shown in Table 8.

Comparative Example 201

The sports shirt made of knitted fabric used in Example 1 was turned inside out, put in a frame so that wrinkles did not form on the back side, and fixed by pinning both shoulders and left and right hems of the shirt.

Next, a sports shirt having the same wiring pattern as that of the Examples was produced by the direct printing method as shown in FIG. 5. First, an underlying layer was screen-printed with the CC paste in a predetermined pattern, the shirt was removed from the frame, dried under predetermined conditions, and set again in the frame. Then, a conductor layer, an insulating cover layer, and an electrode surface layer in this order were each formed by conducting printing, removal from the frame, drying, and fixing again to the frame repeatedly to obtain an electrical wiring. A hook was attached to the obtained sports shirt, and a heart rate sensor WHS-2 manufactured by Union Tool Co. was connected in the same manner as in the Examples, and the evaluation was carried out in the same manner as above. The results are shown in Table 8.

In Comparative Example 201, although the positional gap in the wiring was very large, the wiring of the present invention had a very large width, and the margin when overlaying each layer was also set to about 2 mm, so that no serious problem occurred. However, in the case of a relatively thin wire having a width of less than 1 mm, the positional gap is larger than the width of the wire, so that it is clear that an electrical wiring as designed cannot be formed.

TABLE 8

| | | Example201 | Example202 | Example203 | Example204 | Example205 | Comparative Example201 |
|---|---|---|---|---|---|---|---|
| Wiring configuration | electrode surface layer | CB1 | CB1 | CB1 | CB1 | CB1 | CB1 |
| | insulating cover layer | CC1 | CC1 | CC1 | CC1 | CC1 | CC1 |
| | conductor layer | AG1 | AG22 | AG23 | AG23 | AG23 | AG22 |
| | underlying layer | CC1 | CC1 | CC1 | CC1 | CC1 | CC1 |
| | substrate | knitted fabric | knitted fabric | knitted fabric | knitted fabric | knitted fabric | knitted fabric |
| Wiring formation method | | transfer | transfer | transfer | transfer | transfer | direct printing |
| intermediate medium | | releasing PET | releasing PET | releasing PET | fabric texture type | stripe | Not used |
| positional gap | μm | 54 | 51 | 62 | 76 | 114 | 1680 |
| level difference | | good | good | good | good | good | poor |
| wearing feeling | | good | good | good | very good | good | poor |
| stretching once | maintenance performance of conductivity | good | good | good | good | good | good |
| | insulating property of the insulating cover layer | good | good | good | good | good | good |
| | insulating property of the underlying layer | good | good | good | good | good | good |
| stretching 100 times | maintenance performance of conductivity | good | good | good | good | good | good |
| | insulating property of the insulating cover layer | good | good | good | good | good | good |
| | insulating property of the underlying layer | good | good | good | good | good | good |

INDUSTRIAL APPLICABILITY

As described above, the garment-type electronic device of the present invention includes an electrical wiring composed of a stretchable electrode surface layer, a stretchable insulating cover layer, a stretchable underlying layer, and a stretchable conductive layer, and in addition, the electrical wiring has substantially no level difference at the boundary between the electrode portion and the wiring portion. Therefore, the garment-type electronic device of the present invention has excellent characteristics which satisfy both good electrical characteristics and good wearing feeling.

When seeking the mental state of a wearer particularly based on the physical data of the body such as electrocardiogram data, good wearing feeling makes it possible to make a mental assessment in a more natural state without causing mental noises resulting from poor wearing feeling. Accordingly, the good wearing feeling has great significance in respect of applications of such a garment-type electronic device.

Furthermore, as described above, according to the method for producing the garment-type electronic device of the present invention, it is possible to obtain an excellent garment-type electronic device including an electrical wiring, with improved alignment accuracy, composed of a stretchable electrode surface layer, a stretchable insulating cover layer, a stretchable underlying layer, and a stretchable conductive layer, wherein the electrical wiring has substantially no level difference at the boundary between the electrode portion and the wiring portion, and both good electrical characteristics and good wearing feeling are satisfied.

The present invention is widely applicable, without being limited to the use examples exemplified in the above example, to a wearable device for detecting information of a human body such as bioelectric potential including myoelectric potential and cardiac potential, and biological information including body temperature, pulse, blood pressure, and the like with a sensor or the like provided in a garment; a garment incorporating an electric heating device; a wearable device incorporating a sensor for measuring a clothing pressure; wear that measures a body size by using a clothing pressure and displacement detection; a sock-type device for measuring a pressure of a sole of foot; and the like. Moreover, since the stretchable wiring having no level difference on the surface positively acts also for connection with parts and connectors, the present invention is applicable to a garment in which flexible solar cell modules are integrated in textiles; a wiring part of a tent, bag or the like; a low frequency treatment apparatus having a joint part; a wiring part of a thermal treatment apparatus or the like; a sensing part of degree of flexion, and the like. Such wearable devices can be used for not only a human body but also an animal such as pet or livestock, can be applied to a mechanical device having an expandable portion, a bending portion, and the like, and can also be used as an electrical wiring of a system that is used by connecting a mechanical device such as a robotic prosthetic arm or leg to a human body. In addition, it is also useful as a wiring material for an implant device to be embedded in the body.

Furthermore, the garment-type electronic device of the present invention can collect physical data and vital data of the body as a wearable terminal and transmit the collected data as an electric signal to the outside, and thus serves as an input means for a system for collecting data of each person and providing useful information to a specific person. Moreover, if an actuator is incorporated into the garment-type electronic device of the present invention, it can be applied to assistance functions of exercise such as a power-assisted suit. In addition, by using the garment-type electronic device of the present invention to comprehensively analyze physical data of the body, mental information obtained from vital data, and the like, the garment-type electronic device of the present invention can be used as a terminal of a system to detect and diagnose troubles of the body such as various diseases. Since the garment-type electronic device of the present invention is comfortable in wearing and has no discomfort when wearing it, it is possible to acquire high-quality vital data and hence to use as a data collection device for a system to detect and diagnose not only physical troubles but also mental troubles.

The invention claimed is:

1. A garment-type electronic device comprising an electrical wiring comprising a conductor layer, an insulating cover layer, and an insulating underlying layer in a part in contact with a body surface,
    wherein the conductor layer consists of conductive particles and an elastomer,
    wherein the insulating cover layer consists of an elastomer,
    wherein the insulating underlying layer consists of an elastomer,
    wherein the conductor layer has a first surface, a second surface opposite the first surface, and a side surface between the first surface and the second surface,
    wherein the insulating underlying layer is on a substrate, and the insulating underlying layer is in contact with both the side surface of the conductor layer and the first surface of the conductor layer, the first surface facing the substrate,
    wherein the electrical wiring has substantially no level difference at a boundary between an electrode portion and a wiring portion, and
    wherein the conductor layer, the insulating cover layer, and the insulating underlying layer each have an elongation at break of 50% or more and a tensile elastic modulus of 10 to 500 MPa.

2. The garment-type electronic device comprising an electrical wiring according to claim 1, wherein the electrical wiring comprises the conductor layer, the insulating cover layer, the insulating underlying layer, and an electrode surface layer.

3. The garment-type electronic device according to claim 1,
    wherein the garment-type electronic device can be deformed at a stretching rate of 10% or more without substantially impairing a conductive function of the conductor layer, an insulation function of the insulating cover layer, and an insulation function of the insulating underlying layer.

4. A garment-type electronic device comprising an electrical wiring comprising at least a conductor layer, an insulating cover layer, and an insulating underlying layer in a part in contact with a body surface,
    wherein the conductor layer consists of conductive particles and an elastomer,
    wherein the insulating cover layer consists of an elastomer,
    wherein the insulating underlying layer consists of an elastomer,
    wherein the conductor layer has a first surface, a second surface opposite the first surface, and a side surface between the first surface and the second surface, wherein the insulating underlying layer is on a substrate, and the insulating underlying layer is in contact with both the side surface of the conductor layer and the first surface of the conductor layer, the first surface facing the substrate, wherein a surface of a wiring portion of the electrical wiring has projections and depressions in a shape of fabric texture, and wherein the conductor layer, the insulating cover layer, and the insulating underlying layer each have an elongation at break of 50% or more and a tensile elastic modulus of 10 to 500 MPa.

5. The garment-type electronic device comprising an electrical wiring according to claim 4, wherein the electrical wiring comprises at least the conductor layer, the insulating cover layer, the insulating underlying layer, and an electrode surface layer.

6. The garment-type electronic device according to claim 4, wherein, in the projections and the depressions in the shape of fabric texture on the surface of the wiring portion, a repetition pitch of the projections and the depressions is 0.06 mm or more and 12 mm or less on at least one arbitrary straight line.

7. The garment-type electronic device according to claim 4, wherein, in the projections and the depressions in the shape of fabric texture on the surface of the wiring portion, a difference in height between a concave portion and a convex portion is 7 μm or more and 2500 μm or less.

8. The garment-type electronic device according to claim 4, wherein the garment-type electronic device can be deformed at a stretching rate of 10% or more without substantially impairing a conductive function of the conductor layer, an insulation function of the insulating cover layer, and an insulation function of the insulating underlying layer.

* * * * *